(12) United States Patent
Hong et al.

(10) Patent No.: US 10,213,123 B2
(45) Date of Patent: Feb. 26, 2019

(54) CARDIOVASCULAR MONITORING DEVICE

(71) Applicant: MOCACARE CORP., Palo Alto, CA (US)

(72) Inventors: Wei-Chen Hong, Palo Alto, CA (US); Yinhsuan Chien, Palo Alto, CA (US); Chin-Ling Pai, Palo Alto, CA (US); Maria Bujalska, Palo Alto, CA (US); Yung-Fu Hsu, Palo Alto, CA (US)

(73) Assignee: MOCACARE, CORP., Palo Alto, CA (US)

( * ) Notice: Subject to any disclaimer, the term of this patent is extended or adjusted under 35 U.S.C. 154(b) by 657 days.

(21) Appl. No.: 14/857,947

(22) Filed: Sep. 18, 2015

(65) Prior Publication Data

US 2016/0081572 A1  Mar. 24, 2016

Related U.S. Application Data

(60) Provisional application No. 62/136,570, filed on Mar. 22, 2015, provisional application No. 62/080,412, (Continued)

(51) Int. Cl.
| | |
|---|---|
| *A61B 5/02* | (2006.01) |
| *A61B 5/0404* | (2006.01) |
| *A61B 5/0205* | (2006.01) |
| *A61B 5/145* | (2006.01) |
| *A61B 5/01* | (2006.01) |
| *A61B 5/021* | (2006.01) |

(Continued)

(52) U.S. Cl.
CPC .......... *A61B 5/0404* (2013.01); *A61B 5/0059* (2013.01); *A61B 5/015* (2013.01); *A61B 5/02055* (2013.01); *A61B 5/02141* (2013.01); *A61B 5/11* (2013.01); *A61B 5/14542* (2013.01); *A61B 5/14551* (2013.01); *A61B 5/0456* (2013.01); *A61B 5/746* (2013.01); *A61B 2562/06* (2013.01)

(58) Field of Classification Search
CPC ...... A61B 5/02; A61B 5/0402; A61B 2562/06
See application file for complete search history.

(56) References Cited

U.S. PATENT DOCUMENTS

2006/0009698 A1\*   1/2006   Banet ................... A61B 5/0205
                                                                       600/485
2008/0214942 A1    9/2008   Oh
(Continued)

OTHER PUBLICATIONS

International Search Report and Written Opinion for PCT/US2015/050850, dated Nov. 26, 2015, 14 pages.
(Continued)

*Primary Examiner* — Puya Agahi
(74) *Attorney, Agent, or Firm* — Merchant & Gould P.C.

(57) ABSTRACT

Portable physiological measuring devices and methods are disclosed. Embodiments may provide measurement of blood pressure without traditional blood pressure cuffs. Further, disclosed embodiments may gather pulse oximetry (SpO2), heart rate and body temperature measurements simultaneously. A user's blood pressure index and other vital physiological results may be displayed on a portable physiological measuring apparatus or a portable terminal. Embodiments may provide a portable physiological measuring method and apparatus that displays results on a displayed screen.

13 Claims, 21 Drawing Sheets

Related U.S. Application Data filed on Nov. 17, 2014, provisional application No. 62/052,484, filed on Sep. 19, 2014.

(51) Int. Cl.
| | |
|---|---|
| *A61B 5/11* | (2006.01) |
| *A61B 5/1455* | (2006.01) |
| *A61B 5/00* | (2006.01) |
| *A61B 5/0456* | (2006.01) |

(56) References Cited

U.S. PATENT DOCUMENTS

| | | | |
|---|---|---|---|
| 2012/0022385 A1* | 1/2012 | Shimuta | A61B 5/0404 600/509 |
| 2012/0071734 A1* | 3/2012 | Shimuta | A61B 5/0205 600/301 |
| 2012/0270654 A1 | 10/2012 | Padovani | |
| 2013/0211774 A1 | 8/2013 | Bentley | |
| 2013/0296723 A1* | 11/2013 | Cho | A61B 5/02108 600/501 |
| 2013/0310659 A1* | 11/2013 | Kawachi | A61B 5/0404 600/301 |
| 2014/0012146 A1 | 1/2014 | Fukuda | |
| 2014/0236031 A1 | 8/2014 | Banet et al. | |

OTHER PUBLICATIONS

Yang et al. "Work hours and self-reported hypertension among working people in California." Hypertension, 48 (4):744-750, Oct. 2006.

Allen et al. "Blood pressure trajectories in early adulthood and subclinical atherosclerosis in middle age." JAMA, 311(5):490-497, Feb. 2014.

\* cited by examiner

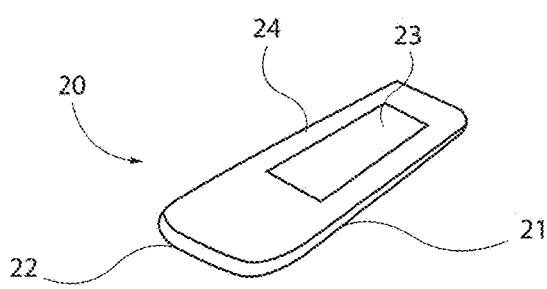
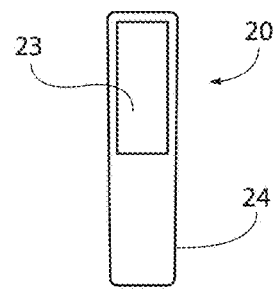
FIG. 2A　　FIG. 2B
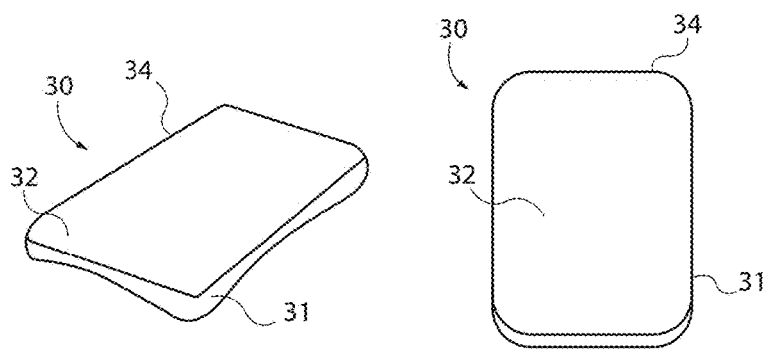
FIG. 3A　　FIG. 3B　　FIG. 3C

CARDIOVASCULAR MONITORING DEVICE

CROSS REFERENCE TO RELATED APPLICATIONS

This application claims priority to U.S. Provisional Application No. 62/052,484, entitled "Blood Pressure Measuring Device Capable of Measuring Electrocardiogram, SPO2, Body Temperature and Activity," filed Sep. 19, 2014 and U.S. Provisional Application No. 62/080,412, entitled "Blood Pressure Index," filed Nov. 17, 2014 and U.S. Provisional Application No. 62/136,570, entitled "Mobile Cardiovascular Monitoring Device Capable of Measuring Electrocardiogram, SPO2, Blood Pressure and Activity," filed Mar. 22, 2015. These referenced Provisional patent applications are hereby incorporated by reference in their entirety into the present patent application.

BACKGROUND OF THE INVENTION

For some hypertension (high blood pressure) risk groups, it may be necessary to monitor blood pressure status frequently, in various locations, and at any number of different times of day. One significant hypertension risk group is elderly individuals (≥65 years old). It has been estimated that 65% of elderly people in the United States have hypertension. Another hypertension risk group is overworked individuals. A study has shown that people who work 51 hours report hypertension 29% more than individuals who work between 11 and 39 hours per week. Yang, et al, Work Hours and Hypertension, Hypertension 48:744-750 (2006). In addition, excessive overwork may increase the risk of sudden death (sometimes known as karōshi death) risk. Obese individuals also have a significantly increased risk of hypertension. In particular, many clinical studies have shown that overweight individuals may have elevated low-density lipoprotein cholesterol and an increased risk of cardiovascular disease.

Regular measurement and evaluation of blood pressure and other physiological parameters is often advised for individuals in these high-risk groups. Current blood pressure measuring devices, however, are not well suited to the task of regular physiological assessment. The standard method for measuring blood pressure is the oscillometric technique. This measurement technique requires the use of a blood pressure cuff on an arm or in another position (such as a wrist or a finger) and may underestimate or overestimate blood pressure, if the cuff is too large or too small. Moreover, incorrect posture may produce inaccurate readings. The excessive pressure produced by a blood pressure cuff during the reading may make the user uncomfortable. In addition, most blood pressure measurement devices are large and need a line to connect the cuff and a measuring apparatus, which makes the device difficult to carry and inconvenient to operate. As a result, cuff-based blood pressure measuring devices are inconvenient and difficult to use for daily measurements.

For example, cuff-type devices may be too large to be carried easily and used regularly, which may limit high-risk individuals to taking physiological measurements only in a hospital or at home. Because these individuals may struggle to monitor and record physiological measurements frequently and in multiple different locations and at different times, they may be unable to take proper precautions and improve their health. Although cuffless, portable physiological measurement devices have been developed, they are often unable to provide accurate blood pressure readings. In addition, while most people know that elevated blood pressure may indicate cardiovascular disease, they do not understand what the measurements mean or how to use the measurements to improve their health.

Therefore, it would be advantageous to have improved devices and methods for measuring blood pressure and, possibly, one or more additional physiological parameters. It would also be advantageous to have devices and methods for providing blood pressure measurement data to a patient in a form that the patient could easily understand and use to improve his or her health. Ideally, such devices would be very portable and easy to use in almost any location, so that a patient could easily measure his or her own blood pressure (and possibly other parameters), without the assistance of a physician or nurse and without needing to go to a hospital or clinic. At least some of these objectives will be addressed by the embodiments described below.

SUMMARY

Embodiments may include a portable physiological measuring apparatus that includes an electrocardiogram circuit unit that uses two electrodes to measure an electrocardiogram signal on the basis of detecting slight physical current through a first electrode and a second electrode. The embodiment may also include a pulse circuit unit including a dual emitter and one detector, to measure dual pulse wave signals and further to derive oxygen saturation from empirical calibration. In addition, the dependency of electrical potential between the first electrode and the second electrode may be determined when the pulse circuit unit is driven without triggering the electrocardiogram circuit unit as a single finger lies on the second electrode, otherwise, the electrocardiogram circuit unit and the pulse circuit unit are both simultaneously used as two portions of a user's body contact the first electrode and the second electrode. The embodiment may also include a first sensor unit configured to sense a movement of a portable physiological measuring apparatus, a signal processing unit configured to receive movement information from the second sensor unit to determine whether to process an electrocardiogram signal and pulse wave signals, and a wireless communication unit configured to transmit the electrocardiogram signal and dual pulse wave signals to a portable terminal. The first sensor unit may also be used to determine the length of the user's arm for follow-up utilization in Pulse Wave Velocity (PWV) calcualtions.

In accordance with another aspect of disclosed embodiments, a method of taking physiological measurements with a portable terminal may include estimating body temperature, heart rate, oxygen saturation and cuff-less blood pressure using received electrocardiogram signals and dual pulse wave signals. Blood pressure estimation may be calculated using a Pulse Arrival Time (PAT) and a Pulse Wave Velocity determined from the electrocardiogram signal and a pulse wave signal. The calculated values may be displayed on a display unit of the apparatus.

In accordance with another embodiment, a method for predicting cardiovascular status in a patient begins by regularly measuring a blood pressure within vessels of the patient as a function of time. From these measured blood pressures, a blood pressure index for a cardiovascular status is derived based on blood pressure. An output based on a blood pressure index is provided. The blood pressure index is determined from the pressure signals sensed from within vessels of the patient. These sensing data may be displayed and stored in the portable terminal. The representative meaning of the recorded blood pressure index over time may assist medical professionals in analyzing cardiovascular status and help treat abnormal blood pressure.

In some embodiments, a portable physiological measuring apparatus for monitoring physiological status of a human or animal subject may include a signal processing unit that receives an electrocardiogram signal and a dual pulse wave signal. The apparatus may calculate a blood pressure value for blood flow based on pressure on a vascular wall and provide an output based on a blood pressure index. The apparatus may further include an electrocardiogram circuit unit on the surface of the apparatus for providing the electrocardiogram signal to the signal processing unit. The apparatus may further include a pulse circuit unit on the surface of the apparatus for providing dual pulse wave signal to the signal processing unit. The signal processing unit may determine the blood pressure index for a pressure of a vascular wall as a function of the systolic and/or diastolic pressure in a blood vessel. The apparatus may further include a first sensor unit that measures body temperature. The apparatus may include a wireless communication unit that transmits the measured electrocardiogram signal, dual pulse wave signals and a body temperature value to a portable terminal. The signal processing unit may output a blood pressure index, SpO2, heart rate, body temperature and measurement results. The portable terminal may calculate a blood flow value, light intensity, heart rate and body temperature using the electrocardiogram signal, dual pulse wave signals and a body temperature value received from the portable physiological measuring apparatus. The portable terminal may output a blood pressure index, SpO2, heart rate, body temperature and measurement results.

In some embodiments, a method for predicting cardiovascular status in a human or animal subject may include calculating a blood pressure value using the calculated pulse transit time and pulse wave velocity; evaluating a encoding number of a blood pressure index based upon blood pressures in a blood vessel; and providing an output based upon the blood pressure index. The blood pressure index may be evaluated by a signal processing unit of a portable physiological measuring apparatus. The blood pressure index may be evaluated by a controller of a portable terminal. The blood pressure index may be displayed by a display unit of a portable physiological measuring apparatus. The method may further include outputting a trend chart of the blood pressure index over time.

In some embodiments, a portable physiological measuring apparatus may include an electrocardiogram circuit unit, including a first electrode and a second electrode included in a surface of a body. The electrocardiogram circuit unit may measure an electrocardiogram signal through the first electrode and the second electrode. The apparatus may also include a pulse circuit unit that includes a dual emitter and a detector included in a surface of a body, which measures a dual pulse wave signal and is integrated at the same position of the second electrode. The apparatus may also include a first sensor unit that senses a movement of the portable physiological measuring apparatus, a signal processing unit that processes the electrocardiogram signal and dual pulse wave signal when it senses that the movement is less than a threshold value, and a storage unit coupled to the signal processing unit that is configured to store the physiological measuring data. The portable physiological measuring apparatus may further include a display unit that displays information associated with measured results. The electrocardiogram circuit unit and the pulse circuit unit may be integrated with the portable physiological measuring apparatus. The portable physiological measuring apparatus may correspond to a mobile device. The mobile device may be a mobile phone. The first electrode may surround or be located near an earpiece area of the mobile phone. The second electrode and the pulse circuit unit may be integrated into a home or other button of the mobile phone. The second electrode and the pulse circuit unit may be located in back of the mobile phone. The first sensor unit may further include a function for measuring the length of a user's arm. The signal processing unit may start measuring the electrocardiogram signal and dual pulse wave signals when the movement is less than the threshold value. The signal processing unit may output a notification associated with a posture during measuring when the movement is greater than or equal to the threshold value. The signal processing unit may output the calculated a blood pressure value, SpO2, heart rate and measurement results. The pulse circuit unit may include a dual photo sensor. The first electrode and the second electrode may have a positive pole and a negative pole respectively. The pulse transit time may be calculated by computing a difference in time between a peak of the electrocardiogram signal and a max-slope point of the pulse wave signal. The pulse wave velocity may be calculated using the pulse transit time and a length of a blood vessel corresponding to a distance from a heart to a point where the pulse wave signal is measured. The length of the blood vessel may be calculated by measuring the distance from a heart to the point where the pulse wave signal is measured, or based on regression equation for different gender, or calculated from the movement and rotation sensor. SpO2 may be based on reflective sensor that starts measurement when a user touches the second electrode of electrocardiogram circuit unit.

In some embodiments, a method of measuring a blood pressure value, SpO2 and heart rate in a portable physiological measuring apparatus may include: receiving an electrocardiogram signal and dual pulse wave signals from an electrocardiogram circuit unit and a pulse circuit unit of a portable physiological measuring apparatus respectively when a blood pressure value, SpO2 and heart rate measurement application is executed; calculating a pulse transit time and a pulse wave velocity using the received electrocardiogram signal and the pulse wave signal; calculating a blood pressure value using the calculated pulse transit time and pulse wave velocity; calculating an SpO2 value using dual pulse wave signals; calculating a heart rate value using R-R interval of an electrocardiogram signal; and outputting the calculated blood pressure, SpO2, heart rate and measurement results.

The pulse transit time may be calculated by computing a difference in time between a peak of the electrocardiogram signal and a max-slope point of the pulse wave signal. The pulse wave velocity may be calculated by the pulse transit time and a length of a blood vessel corresponding to a distance from a heart to the point where the pulse wave signal is measured (such as a fingertip). The length of the blood vessel may be calculated by measuring the distance from a heart to the point where the pulse wave signal is measured, or based on a regression equation for different gender, or calculated from movement and rotation sensor. The SpO2 value may be calculated by dual pulse wave signals. The heart rate may be calculated by an electrocardiogram signal or a pulse wave signal. Receiving the electrocardiogram signal and dual pulse wave signals from the portable physiological measuring apparatus may include measuring the electrocardiogram signal through an electrocardiogram circuit unit including a first electrode and a second electrode included in a surface of a body of the portable physiological measuring apparatus; measuring dual pulse wave signals through pulse circuit unit located on the same position of the second electrode; and receiving the measured electrocardiogram signal and dual pulse wave signals.

The method may further include sensing a movement of the portable physiological measuring apparatus during measuring the electrocardiogram and dual pulse wave signals; and starting measuring the electrocardiogram signal and dual pulse wave signals when it is sensed that the movement is less than a threshold value. The method may further include stopping measuring the electrocardiogram signal and dual pulse wave signals when the movement is greater than or equal to a threshold value.

In some embodiments, a portable physiological measuring apparatus may include an electrocardiogram circuit unit that has a first electrode and a second electrode disposed on a surface of the apparatus that measures an electrocardiogram signal through the first electrode and the second electrode. The apparatus may also include a pulse circuit unit, including a dual emitter and a detector that measures dual pulse wave signals and is integrated at the same position of the second electrode. The apparatus may also include a first sensor unit that measures body temperature and is integrated at the same position as the first electrode. The apparatus may also include a second sensor unit that measures the length of the user's arm and senses a movement of the portable physiological measuring apparatus and a signal processing unit that processes the electrocardiogram signal, dual pulse wave signals, and a body temperature value when it senses that the movement is less than a threshold value. The apparatus may also include a wireless communication unit that transmits the measured electrocardiogram signal, dual pulse wave signals and a body temperature value to a portable terminal that measures a blood pressure value, SpO2, heart rate and body temperature using the measured electrocardiogram signal, dual pulse wave signals and a body temperature value.

The signal processing unit may start measuring the electrocardiogram signal, dual pulse wave signals and a body temperature value when the movement is less than the threshold value. The signal processing unit may output a notification associated with the user's posture during the measurements when the movement is greater than or equal to the threshold value. The signal processing unit may output the calculated blood pressure value, SpO2, heart rate, body temperature and measurement results. The pulse circuit unit may correspond to a dual photo sensor.

The first electrode and the second electrode may have a positive pole and a negative pole respectively. The first sensor unit may correspond to a thermal sensor or a photon sensor. The portable terminal may calculate a blood pressure value, SpO2, heart rate and body temperature using the electrocardiogram signal, dual pulse wave signals and a body temperature value received from the portable physiological measuring apparatus. The portable terminal may output the calculated blood pressure value, SpO2, heart rate, body temperature and measurement results. The pulse transit time may be calculated by calculating a difference in time between a peak of the electrocardiogram signal and a max-slope point of the pulse wave signal. The pulse wave velocity is calculated by the pulse transit time and a length of a blood vessel corresponding to a distance from a heart to a point where the pulse wave signal is measured. The length of the blood vessel may be calculated by measuring the distance from the user's heart to the point where the pulse wave signal is measured, or based on regression equation for different gender, or calculated from the movement and rotation sensor. SpO2 may be based on reflective sensor that starts measurement when a user touches the second electrode of electrocardiogram circuit unit.

An embodiment of a method for measuring a blood pressure value, SpO2, heart rate, body temperature in a portable terminal, the method may include: receiving an electrocardiogram signal, dual pulse wave signals, and a body temperature value from a portable physiological measuring apparatus when a measurement application is executed; calculating a pulse transit time and a pulse wave velocity using the received electrocardiogram signal and the pulse wave signal; calculating a blood pressure value using the calculated pulse transit time and pulse wave velocity; calculating an SpO2 value using dual pulse wave signals; calculating a heart rate value using R-R interval of an electrocardiogram signal; calculating a body temperature value using thermal sensor; and outputting the calculated blood pressure, SpO2, heart rate, body temperature value and measurement results.

The pulse transit time may be calculated by computing a difference in time between a peak of the electrocardiogram signal and a max-slope point of the pulse wave signal.

The pulse wave velocity may be calculated by the pulse transit time and a length of a blood vessel corresponding to a distance from a heart to the point where the pulse wave signal is measured. The length of the blood vessel may be calculated by measuring the distance from a heart to the point where the pulse wave signal is measured, or based on regression equation for different gender, or calculated from movement and rotation sensor. The SpO2 value may be calculated by dual pulse wave signals. The heart rate may be calculated by an electrocardiogram signal or a pulse wave signal. The body temperature value may be calculated using an infrared signal. Receiving the electrocardiogram signal, dual pulse wave signals and a body temperature value from the portable physiological measuring apparatus may include: measuring the electrocardiogram signal through an electrocardiogram circuit unit including a first electrode and a second electrode included in a surface of a body of the portable physiological measuring apparatus; measuring dual pulse wave signals through pulse circuit unit located on the same position of the second electrode; measuring a body temperature value through the first sensor unit located on the same position of the first electrode; and receiving the measured electrocardiogram signal, dual pulse wave signals and a body temperature value. The method may further include sensing a movement of the portable physiological measuring apparatus during measuring the electrocardiogram, dual pulse wave signals and a body temperature value; and starting measuring the electrocardiogram signal, dual pulse wave signals and a body temperature value when it is sensed that the movement is less than a threshold value. The method may further include stopping measuring the electrocardiogram signal, dual pulse wave signals and a body temperature value when the movement is greater than or equal to a threshold value.

In some embodiments, a portable physiological measuring apparatus for measuring at least one physiological parameter of a user may include a housing and an electrocardiogram circuit coupled with the housing. The electrocardiogram circuit may include an electrode disposed at a location on a surface of the housing and configured to measure an electrocardiogram signal. The apparatus may also include a pulse circuit coupled with the housing and including a dual emitter and a detector, the pulse circuit configured to measure a dual pulse wave signal; an arm-length/motion sensor coupled with the housing and configured to measure a length of an arm of the user and sense movement of the apparatus; and a signal processing unit coupled with the housing. The signal processing unit may be configured to measure the electrocardiogram signal and the dual pulse wave signal using the electrocardiogram circuit and the pulse circuit responsive to determining that movement of the apparatus sensed by the arm-length/motion sensor is below a threshold value.

The detector of the pulse circuit may be disposed on the surface of the housing at the location. The apparatus may further include a body temperature sensor disposed on the surface of the housing at the location. The apparatus may further include a wireless communication unit coupled with the housing and configured to transmit the measured electrocardiogram signal and the measured dual pulse wave signal to a portable terminal. The portable terminal may be configured to calculate a blood pressure value, an SpO2 value, a heart rate value, and a body temperature value using the measured electrocardiogram signal, the dual pulse wave signal, and a body temperature value measured using the body temperature sensor. The apparatus may further include a processor configured to determine at least one of a blood pressure value, an SpO2 value, or a heart rate value using the measured electrocardiogram signal and the measured dual pulse wave signal. The signal processing unit may be further configured to provide a posture notification to the user responsive to determining that movement of the apparatus sensed by the arm-length/motion sensor is above the threshold value. The pulse circuit may be selected from a group consisting of a dual photo sensor, a thermal sensor, and a photon sensor.

In some embodiments, a method of measuring a blood pressure value of a user using a portable physiological measuring apparatus may include: receiving an electrocardiogram signal from an electrocardiogram of a portable physiological measuring apparatus; receiving a dual pulse wave signal from a pulse circuit unit of the portable physiological measuring apparatus; calculating a pulse transit time and a pulse wave velocity using the received electrocardiogram signal and the received pulse wave signal; calculating the blood pressure value using the calculated pulse transit time and the calculated pulse wave velocity; and outputting the calculated blood pressure to the user.

The method may further include calculating an SpO2 value using the dual pulse wave signal. The method may further include calculating a heart rate value using an R-R interval of the electrocardiogram signal. Calculating the pulse transit time may include computing a difference in time between a peak of the electrocardiogram signal and a max-slope point of the pulse wave signal. The pulse wave velocity may be calculated using the pulse transit time and a length of a blood vessel of the user corresponding to a distance from a heart of the user to a point where the pulse wave signal is measured. The length of the blood vessel may be calculated using a regression equation. The length of the blood vessel may be calculated using a movement and rotation sensor. The method may further include calculating a heart rate value using at least one of the electrocardiogram signal or the dual pulse wave signal. Receiving the electrocardiogram signal and the dual pulse wave signal from the portable physiological measuring apparatus may include measuring the electrocardiogram signal through an electrocardiogram circuit unit including a first electrode and a second electrode included in a surface of the portable physiological measuring apparatus; measuring the dual pulse wave signal through pulse circuit unit located on the same position as the second electrode; and receiving the measured electrocardiogram signal and the dual pulse wave signal. The method may further include sensing a movement of the portable physiological measuring apparatus and measuring the electrocardiogram signal and the dual pulse wave signal responsive to determining that the movement is less than a threshold value. The method may further include stopping measuring the electrocardiogram signal and dual pulse wave signal responsive to determining that the movement is greater than or equal to a threshold value.

In some embodiments, a portable physiological measuring apparatus may include an electrocardiogram circuit configured to measure an electrocardiogram signal; a pulse circuit configured to measure a dual pulse wave signal; a sensor cluster at a first location including the electrocardiogram circuit and the pulse circuit; and a processor. The processor may be configured to receive the electrocardiogram signal and the dual pulse wave signal; calculate a pulse transit time and a pulse wave velocity using the measured electrocardiogram signal and the measured pulse wave signal; calculate a blood pressure value using the calculated pulse transit time and the calculated pulse wave velocity; and output the calculated blood pressure. The sensor cluster may be disposed at a first end of the apparatus.

BRIEF DESCRIPTION OF THE DRAWINGS

FIG. 2A illustrates a perspective view of an embodiment of a portable physiological measuring apparatus.

FIG. 2B illustrates a top view of the embodiment of FIG. 2A.

FIG. 3A illustrates a bottom view of an embodiment of a portable physiological measuring apparatus.

FIG. 3B illustrates a bottom view of the embodiment of FIG. 3A.

FIG. 3C illustrates a top view of the embodiment of FIG. 3A.

DETAILED DESCRIPTION

Disclosed embodiments generally relate to portable physiological measuring apparatuses and methods for measuring blood pressure of a user and determining, from the blood pressure measurement, a blood pressure index for the user. The blood pressure index may be easily understandable by a layperson user and may be used as a predictor of cardiovascular disease or failure. In addition to measuring blood pressure, various embodiments may advantageously measure one or more other physiological parameters of the user.

Disclosed embodiments are generally small, portable, non-invasive, comfortable to wear or carry, easy to use and readily available devices that facilitate home- and self-measuring of physiological parameters. The convenience of the embodiments disclosed herein has numerous advantages over traditional physiological measuring devices and techniques, including decreased cost and increased patient compliance, especially when measuring physiological signals over long periods of time.

Figure 1A:
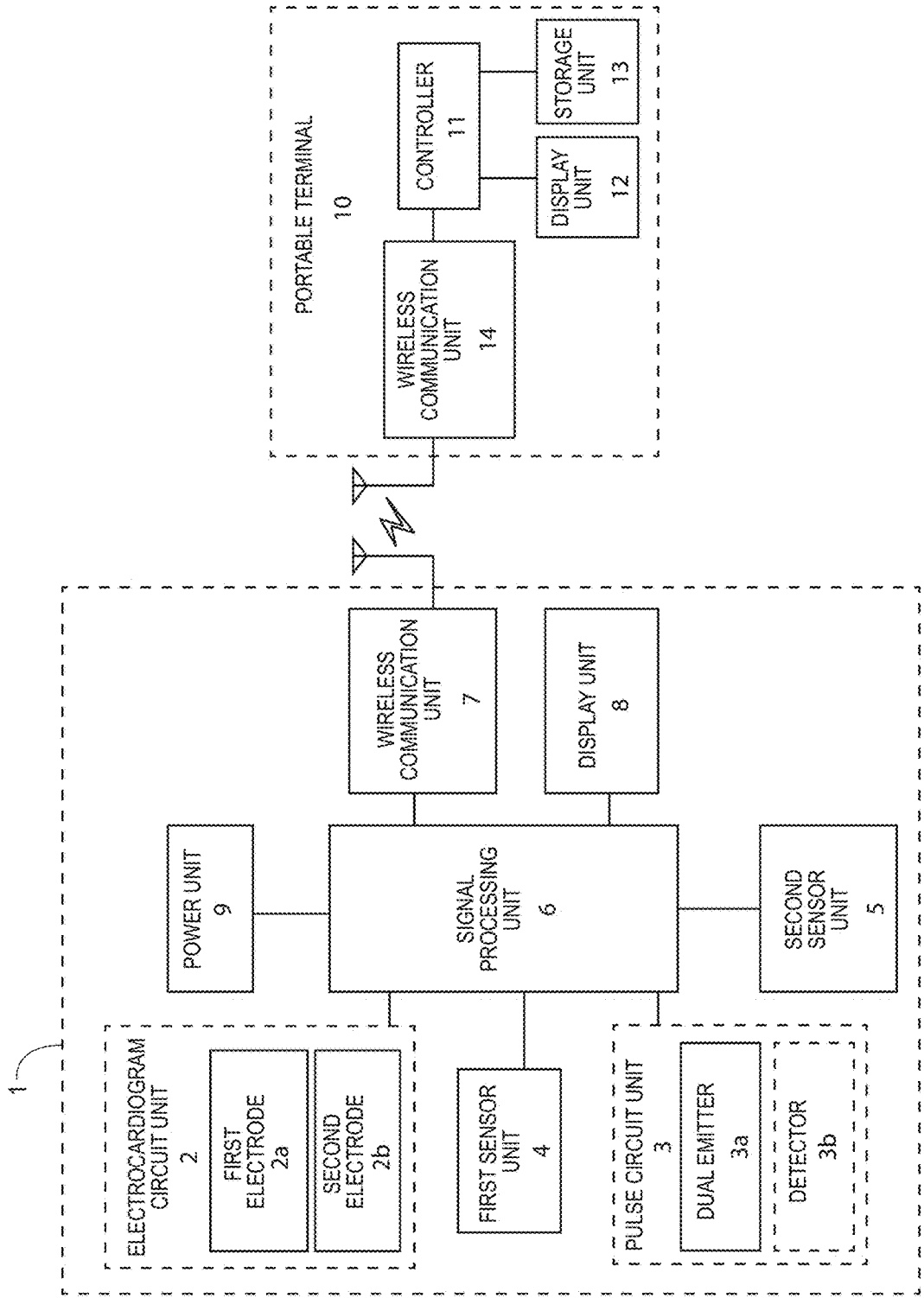
FIG. 1A illustrates a block diagram of an embodiment of a portable physiological measuring apparatus and a portable terminal.

FIG. 1A is a block diagram of one embodiment of a portable physiological measuring system, including a portable physiological measuring apparatus 1 that wirelessly communicates with a portable terminal 10. The portable physiological measuring apparatus 1 may be a wireless and cuffless portable measuring apparatus. The portable physiological measuring apparatus 1 may be included in a portable phone, a portable monitor, a portable accessory, a digital archives player, a portable terminal case or other suitable devices. The portable physiological measuring apparatus 1 may be an accessory attached to the portable terminal 10. The portable terminal 10 may be included in a mobile phone, a smart phone, a tablet, a personal computer, a notebook, a digital sound source playback apparatus, a portable multimedia player, a hospital equipment unit, or any device that is capable of transceiving data through communication with the portable physiological measuring apparatus 1.

The portable physiological measuring apparatus 1 may include an electrocardiogram circuit unit 2, a pulse circuit unit 3, a first sensor unit 4, a second sensor unit 5, a signal processing unit 6, a wireless communication unit 7, a display unit 8, and a power unit 9. The signal processing unit 6 may be a controller.

The electrocardiogram circuit unit 2 may include a first electrode 2a and a second electrode 2b that have different polarities from each other. For example, the first electrode 2a may have a positive (+) potential, and the second electrode 2b may have a negative (−) potential. The electrodes 2a and 2b may be configured to be placed in contact with a portion of a user's body (such as a finger, an arm, a hand, a wrist, a head, or a leg) to measure an electrocardiogram signal from among bio-signals.

The electrocardiogram circuit unit 2 may measure an electrocardiogram signal associated with a change, over time, in an action potential of a cardiac muscle cell generated based on a heartbeat, using a potential difference of the first electrode 2a and the second electrode 2b.

The electrocardiogram circuit unit 2 may be integral to the cuffless portable physiological measuring apparatus 1 and be in direct contact with a portion of a user's body. The electrocardiogram circuit unit 2 may measure an electrocardiogram signal and transmit the signal to the signal processing unit 6.

The electrocardiogram circuit unit 2 may measure an electrocardiogram signal when the first electrode 2a and the second electrode 2b are placed in contact with a portion of the body of the user, and the circuit 2 may transmit the measured signal to the signal processing unit 6. The electrocardiogram circuit unit 2 may detect pressure or use other means to determine whether sufficient contact is made between the electrodes 2a, 2b and the user's skin.

The pulse circuit unit 3 may be configured with a dual emitter 3a and a detector 3b. The pulse circuit 3, dual emitter 3a, and detector 3b may be put in the same position as an electrode (e.g., the second electrode 2b). Being put in the same position as an electrode may mean that a user's finger could cover both a portion of the pulse circuit 3 and an electrode. The pulse circuit unit 3 may be in contact with a portion of the body of the user, such as a finger, and measure dual pulse wave signals and transmit the measured signals to the signal processing unit 6.

The electrocardiogram circuit unit 2 and the pulse circuit unit 3 may be disposed on an external surface of the portable physiological measuring apparatus 1 or may otherwise be configured to be in direct contact with a portion of the body of the user during use.

The first sensor unit 4 may be a thermal sensor or a photon sensor in contact with a portion of the user's body. The first sensor unit 4 may be configured to measure the temperature of the user and may be located in the same position as an electrode (e.g., the first electrode 2*a*), relative to the apparatus 1.

The second sensor unit 5 may be a combined arm-length/motion sensor, configured to calculate the length of a user's arm and sense a motion of the portable physiological measuring apparatus 1. The second sensor unit 5 may be a sensor internal to the apparatus 1, such as an accelerometer, a gyroscope, a shock sensor, a tilt sensor, an altimeter, a gravity sensor, a terrestrial magnetism sensor, combinations thereof, or another type of a sensor that is configured to sense movement or a tilt of the portable physiological measuring apparatus 1. The second sensor unit 5 may collect and then transmit a corresponding motion signal to the signal processing unit 6. The motion signals may be used to measure the user's arm length.

The signal processing unit 6 may be included in the portable physiological measuring apparatus 1 and control general operations and conditions of component elements of the portable physiological measuring apparatus 1. When power is supplied through the power unit 9, the signal processing unit 6 may begin to operate when a contact or a press is sensed by the electrocardiogram circuit unit 2 or the pulse circuit unit 3. A contact or press may occur, for example, when a user places a finger on a sensor. When a contact or a press is sensed by the electrocardiogram circuit unit 2, the signal processing unit 6 may perform primary signal processing on an electrocardiogram signal and dual pulse wave signals corresponding to physiological signals received from the electrocardiogram circuit unit 2 and the pulse circuit unit 3 for communication with the portable terminal 10. The electrocardiogram circuit unit 2 may transmit the signal to the portable terminal 10 through the wireless communication unit 7, or independently calculate the electrocardiogram signal and dual pulse wave signals, and cause the display of physiological information (such as blood pressure, SpO2, heart rate and body temperature) on the display unit 8.

When a contact or a press on the first and/or the second electrode is sensed, the signal processing unit 6 may calculate a movement value associated with a degree of a tilt or a distance of a movement based on a signal received from the second sensor unit 5. When the calculated movement value is under a threshold value, measurement of the electrocardiogram signal and the pulse wave signal may be started, and the signal processing unit 6 processes an electrocardiogram signal and a pulse wave signal. When the user is moving or tilted during the measurement and causes a calculated movement value higher than or equal to a threshold value, then the signal processing unit 6 may be configured to not process the physiological signals. When the second sensor unit 5 senses the movement of the user, guiding information or an alarm may appear on the display unit 8 or via an audio signal, to guide the user to maintain a steady posture during measurement. This may improve accuracy of the apparatus's measurements.

The wireless communication unit 7 may perform a communication function between the portable physiological measuring apparatus 1 and the portable terminal 10. The wireless communication unit 7 may transmit physiological signal information and instructions to the portable terminal 10. The physiological situation of the user may be evaluated, and the user may receive the result. The wireless communication unit 7 may be configured to wirelessly communicate with other devices, using a wireless technology such as but not limited to Bluetooth®, Zigbee®, Near Field Communication (NFC), Wireless Local Area Network (WLAN) and/or Wi-Fi®.

The display unit 8 may display information associated with operation of the portable physiological measuring apparatus 1. For example, the display unit 8 may display information associated with measuring an electrocardiogram signal and a pulse wave signal. When the portable physiological measuring apparatus 1 is light-weight and small, the size of the display unit 8 may be relatively small. The display unit 8 may use liquid crystal display technology, light emitting diode technology, E-Ink technology, and/or any other display technology capable of displaying data received from the signal processing unit 6. Various screens of information associated with a measurement result obtained by the portable physiological measuring apparatus 1 may be output through a display unit 12 of the portable terminal 10.

When the signal processing unit 6 of the portable physiological measuring apparatus 1 uses an electrocardiogram signal and dual pulse wave signals to support a function of calculating a blood pressure, SpO2, and heart rate value, the display unit 8 may also display the physiological measurement results simultaneously.

The portable terminal 10 may include a controller 11, the display unit 12, a storage unit 13, and a wireless communication unit 14. The controller 11 may be configured to decode the signal from the wireless transmitter, display the physiological information on the display unit 12, and provide the final results to the storage unit 13. The controller 11 may be configured to calculate blood pressure, SpO2, and heart rate values, using an electrocardiogram signal and dual pulse wave signals received from the portable physiological measuring apparatus 1. The blood pressure value may be calculated using Pulse Transit Time (PTT) and a Pulse Wave Velocity (PWV) from receiving the electrocardiogram signal and one of pulse wave signals. The SpO2 value may be evaluated by using dual pulse wave signals.

The display unit 12 may display one or more physiological parameter values, such as but not limited to a blood pressure index, SpO2, heart rate, and body temperature, calculated by the electrocardiogram signal and dual pulse wave signals. The display unit 12 may also display one or more additional readings that indicate and/or explain the user's health condition. In addition to the above functions, the display unit 12 may also display health educational information, self-assessment records, a tailored exercising program, information regarding emergency services in the vicinity of the user and/or other information. In some embodiments, the display unit 12 may also display any suitable information associated with conditions and operations of the portable terminal 10 and the portable physiological measuring apparatus 1, based on controlling the controller 11.

The storage unit 13 may store the measurements and related information from the controller 11 or elsewhere. The storage unit 13 may be included in a disk or a memory card (such as SD, CF, XD, mini card, or other formats) constructed in the portable terminal 10. For example, the storage unit 13 may continuously store calculated physiological parameter values, and the user or medical personnel can evaluate the health condition using these parameters.

The wireless communication unit 14 may wirelessly transmit instruction or data from the controller 11 and/or may wirelessly receive data from the portable physiological measuring apparatus 1, in order to transfer the data to the controller 11 of the portable terminal 10.

Figure 1B:
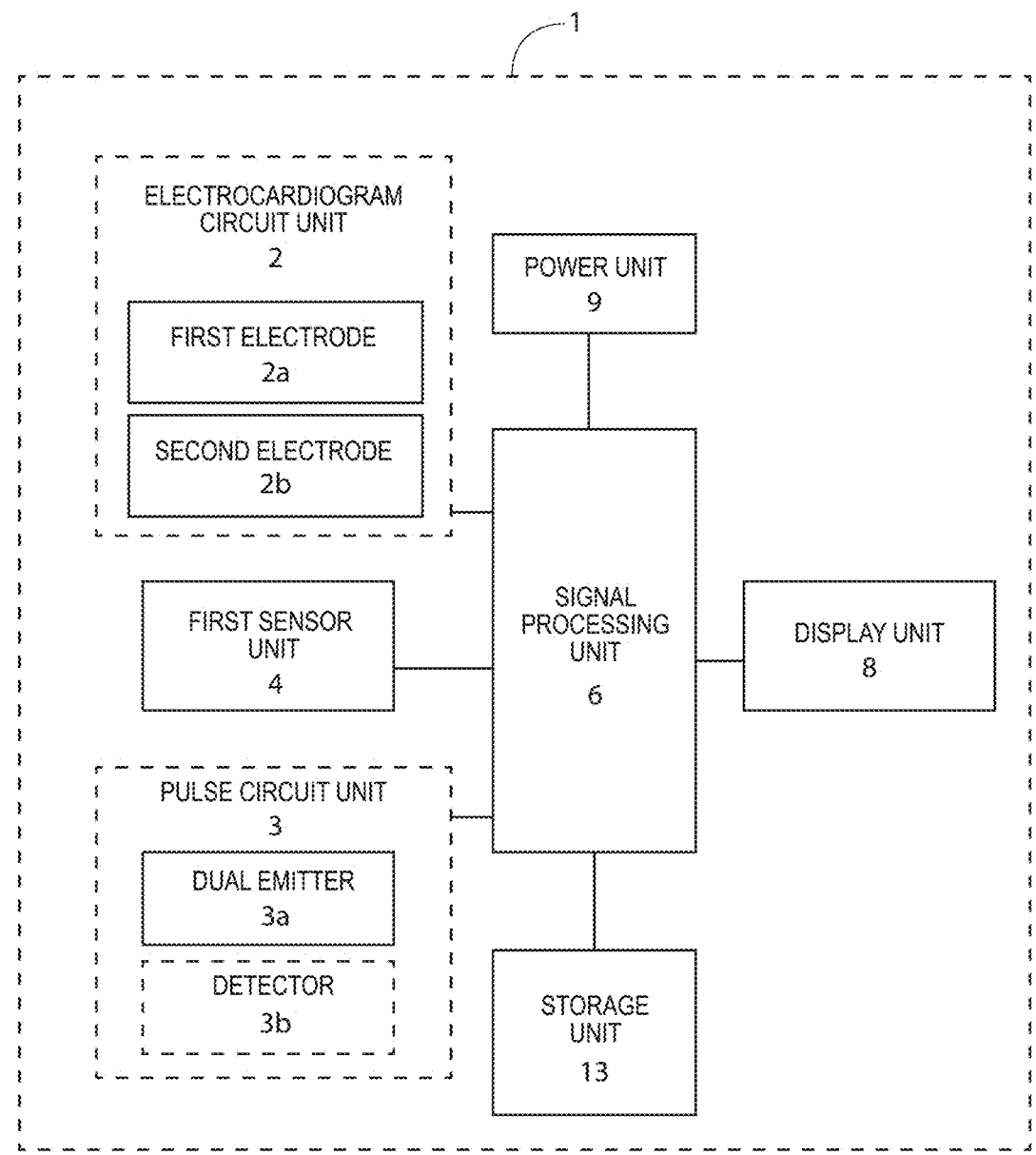
FIG. 1B illustrates a block diagram of an embodiment of a portable physiological measuring apparatus.

FIG. 1B illustrates an alternative embodiment of the device of FIG. 1A without the portable terminal 10. In this embodiment, the device may be integrated into a mobile device, such as a mobile phone. As illustrated, the device includes a storage unit 13 on the apparatus 1 for storing final results. In this embodiment, the first sensor unit 4 fulfills the role of the second sensor unit 5 of the device of FIG. 1A.

FIGS. 2A-14 illustrate various embodiments of a portable physiological measuring apparatus as just described. The portable physiological measuring apparatus may be constructed as a flat-shaped object, a cylinder, a cuboid, a hexagonal prism, a triangular prism, have a curved shape, and/or have other shapes and configurations. In general, each embodiment of the physiological measuring apparatus includes a housing, and the various components described above are coupled with and/or incorporated into the housing—either located within the housing, disposed on a surface of the housing, incorporated into a portion of the housing, or a combination thereof.

FIGS. 2A and 2B illustrate one embodiment of a physiological measuring apparatus 20, which includes a housing 24 with a slim, elongate design. Coupled with the housing 24 are a first sensor unit and/or first electrode 21, a pulse circuit unit and/or second electrode 22, and a display unit 23. The first electrode 21 may be located on a lateral side surface of the housing 24, and the second electrode 22 may be located on a bottom side surface of the device.

FIGS. 3A-3C are rear perspective, rear, and front perspective views of an alternative embodiment of a physiological measuring apparatus 30, including a housing 34 with a rectangular and less elongate configuration than the embodiment described immediately above. A first electrode 31 may be located on a lateral side surface of the housing 34, and in fact may extend along one entire lateral side surface or even multiple lateral sides or the entire perimeter of the housing 34. An entire rear surface of the housing 34, or a portion thereof in alternative embodiments, may be covered by a second electrode 32. A front surface of the device may include a display 33.

Figure 4:
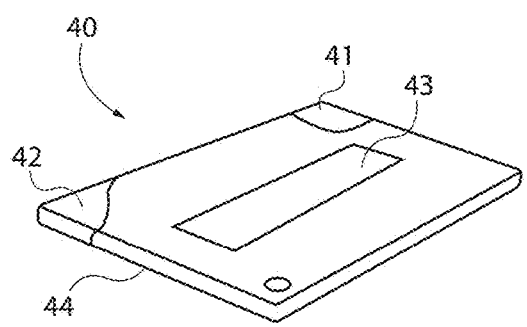
FIG. 4 illustrates a perspective view of an embodiment of a portable physiological measuring apparatus.

FIG. 4 is a perspective view of another alternative embodiment of a portable physiological measuring apparatus 40. This embodiment may include a housing 44, an elongate display 43, a first electrode 41 at or near one corner, and a second electrode 42 at or near another corner.

Figure 5:
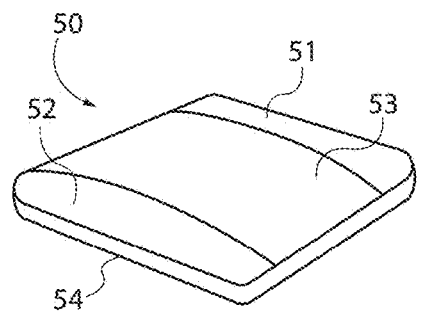
FIG. 5 illustrates a perspective view of an embodiment of a portable physiological measuring apparatus.

FIG. 5 is a perspective view of another alternative embodiment of a portable physiological measuring apparatus 50. This embodiment may include a first electrode 51, a second electrode 52, an elongate display 53, and a housing 54. The first and second electrodes 51 and 52 may be disposed on opposite edges of the apparatus 50. The display 53 may be disposed between the first and second electrodes 51 and 52.

Figure 6A:
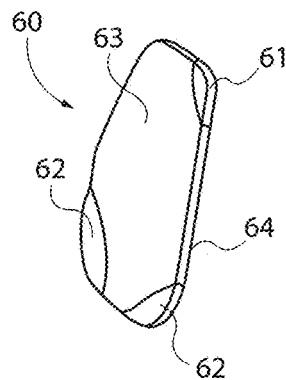
FIG. 6A illustrates a perspective view of an embodiment of a portable physiological measuring apparatus.
Figure 6B:
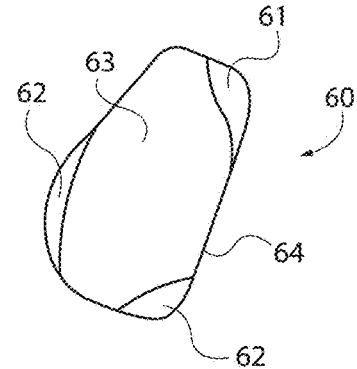
FIG. 6B illustrates an alternative perspective view of the embodiment of FIG. 6A.

FIGS. 6A and 6B are perspective views of another alternative embodiment of a portable physiological measuring apparatus 60. This embodiment may include at least three separate electrodes 61 and 62, a display 63, and a housing 64. The display 63 may be disposed between the electrodes 61, 62.

Figure 7:
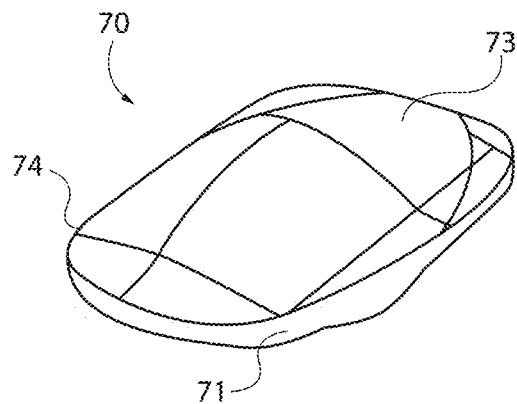
FIG. 7 illustrates a perspective view of an embodiment of a portable physiological measuring apparatus.

FIG. 7 is a perspective view of another embodiment of a portable physiological measuring apparatus 70. The apparatus 70 may include a tortoise-shell shaped housing 74 having an electrode 71 on a side thereof and a display 73 disposed on a curved portion thereof.

Figure 8:
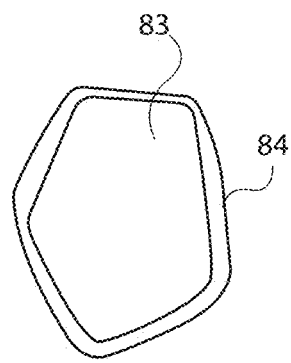
FIG. 8 illustrates a perspective view of an embodiment of a portable physiological measuring apparatus.
Figure 9:
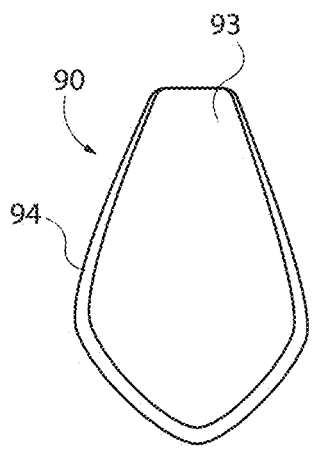
FIG. 9 illustrates a perspective view of an embodiment of a portable physiological measuring apparatus.

FIGS. 8 and 9 are perspective views of other embodiments of portable physiological measuring apparatuses 80, 90 having a display 83, 93. Housings 84, 94 may have the shape of a rounded pentagon. The embodiments shown in FIGS. 8 and 9 may have electrodes disposed in various regions on the housing 84, 94.

Figure 10:
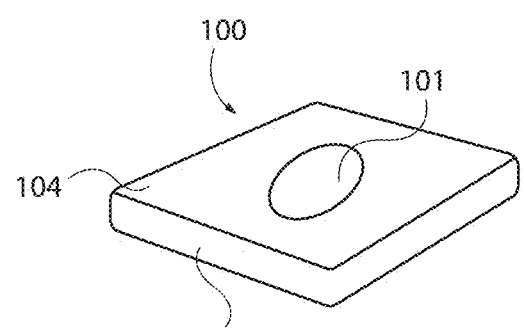
FIG. 10 illustrates a perspective view of an embodiment of a portable physiological measuring apparatus.

FIG. 10 is a perspective view of another embodiment of a portable physiological measuring apparatus 100. The apparatus 100 has a housing 104 in the shape of a rectangle having rounded corners, a circular first electrode 101 on a face of the housing 14 and a second electrode 102 on at least one side of the apparatus 100.

Figure 11:
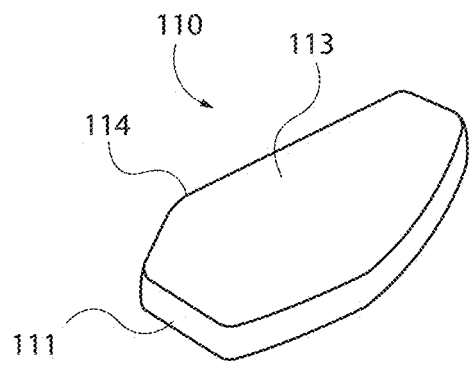
FIG. 11 illustrates a perspective view of an embodiment of a portable physiological measuring apparatus.

FIG. 11 is a perspective view of another embodiment of a portable physiological measuring apparatus 110. The apparatus 110 includes an electrode 111 and a display 113 disposed on or in a housing 114.

Figure 12A:
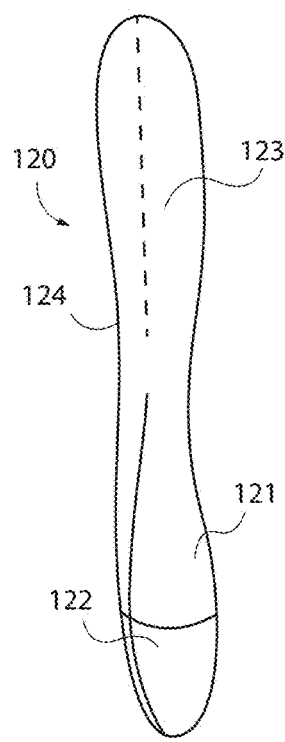
FIG. 12A illustrates a perspective view of an embodiment of a portable physiological measuring apparatus.
Figure 12B:
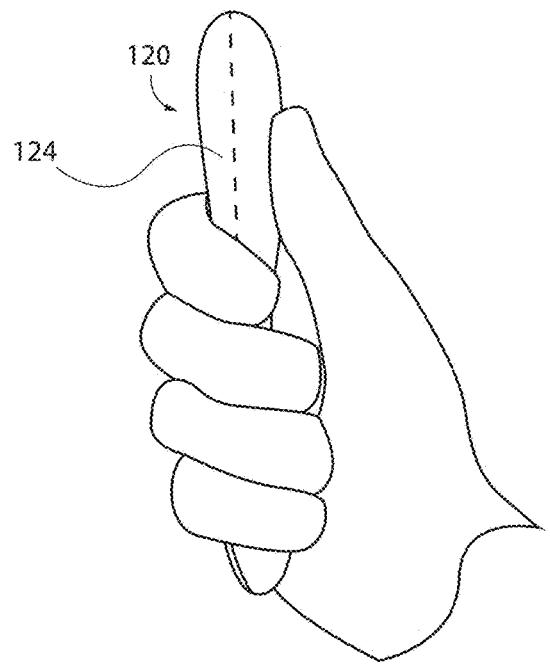
FIG. 12B illustrates a perspective view of the embodiment of FIG. 12A being held in a hand.

FIG. 12A is a perspective view of another embodiment of a portable physiological measuring apparatus 120. The apparatus 120 has an elongate housing 124 and includes electrodes 121, 122 on a first end of the housing 124 and a display 123 on a second end of the housing 124 opposite the first end. FIG. 12B illustrates a perspective view of the embodiment 120 of FIG. 12A being held in a hand, such that electrodes 121, 122 are in contact with the hand and the display 123 is visible to a viewer.

Figure 13A:
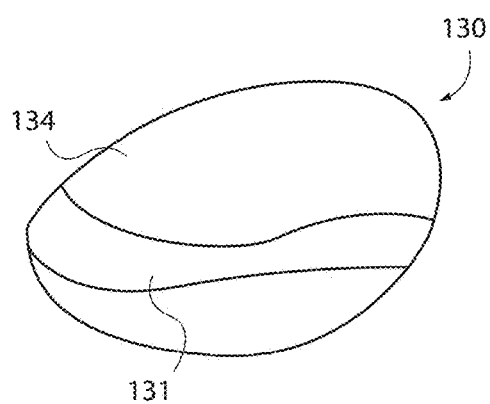
FIG. 13A illustrates a perspective view of an embodiment of a portable physiological measuring apparatus.
Figure 13B:
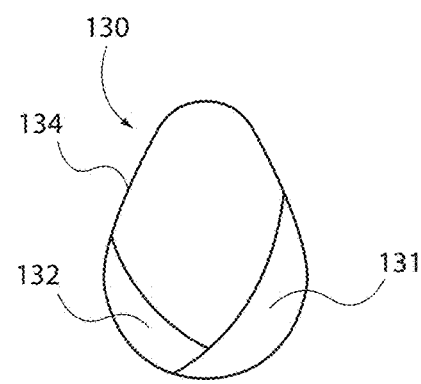
FIG. 13B illustrates a rear view of an embodiment of a portable physiological measuring apparatus.

FIGS. 13A and 13B are perspective views of another embodiment of a portable physiological measuring apparatus 130. The apparatus 130 has a substantially egg-shaped housing 134 and includes a first curved electrode strip 131 and a second curved electrode strip 132 extending along the length of the housing 134 of the apparatus 130. The electrode strips 131, 132 may be configured such that if a user holds the device in a cupped hand or hands, the electrode strips 131, 132 will be in contact with the user.

Figure 14A:
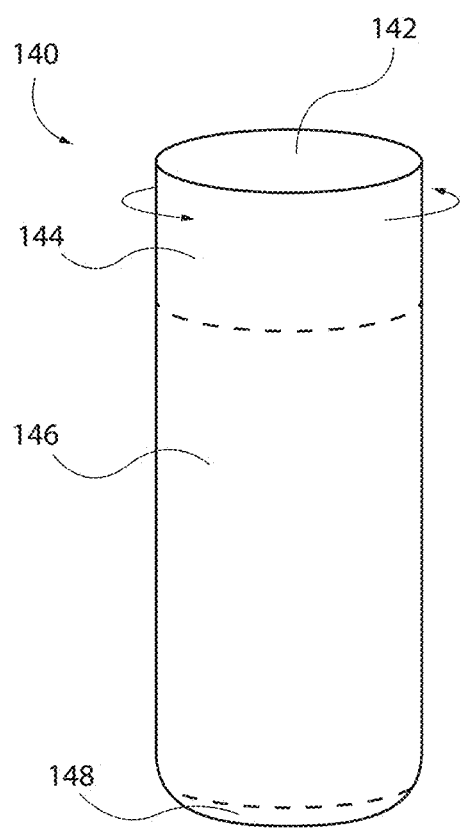
FIG. 14A illustrates a perspective view of an embodiment of a portable physiological measuring apparatus.
Figure 14B:
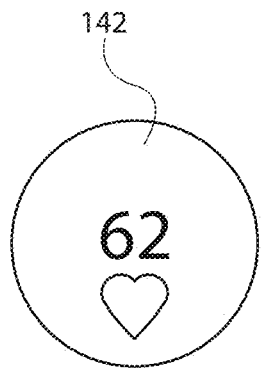
FIG. 14B illustrates a top view of the embodiment of FIG. 14A.
Figure 14C:
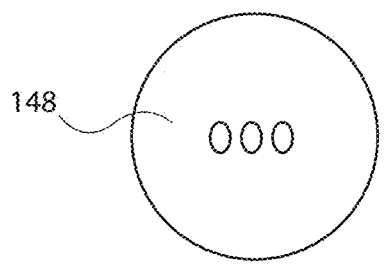
FIG. 14C illustrates a bottom view of the embodiment of FIG. 14B.

FIGS. 14A, 14B, and 14C are perspective, top and bottom views, respectively, of another alternative embodiment of a portable physiological measuring apparatus 140. This embodiment of the apparatus 140 includes a display 142, a head 144, a body 146, and a sensor 148. The display 142 may be mounted on the head 144 of the apparatus and may be configured to provide information relating to the operation of the apparatus to the user. The head 144 may rotate relative to the body 146 to provide functionality for selecting options or otherwise provide input from the user to the apparatus. The body 146 may be an elongate, cylindrical portion of the apparatus. The sensor 148 may be located on end of the apparatus opposite the head 144. The sensor 148 may include an electrode or otherwise be adapted to receive or monitor physiological information relating to a user.

Figure 15:
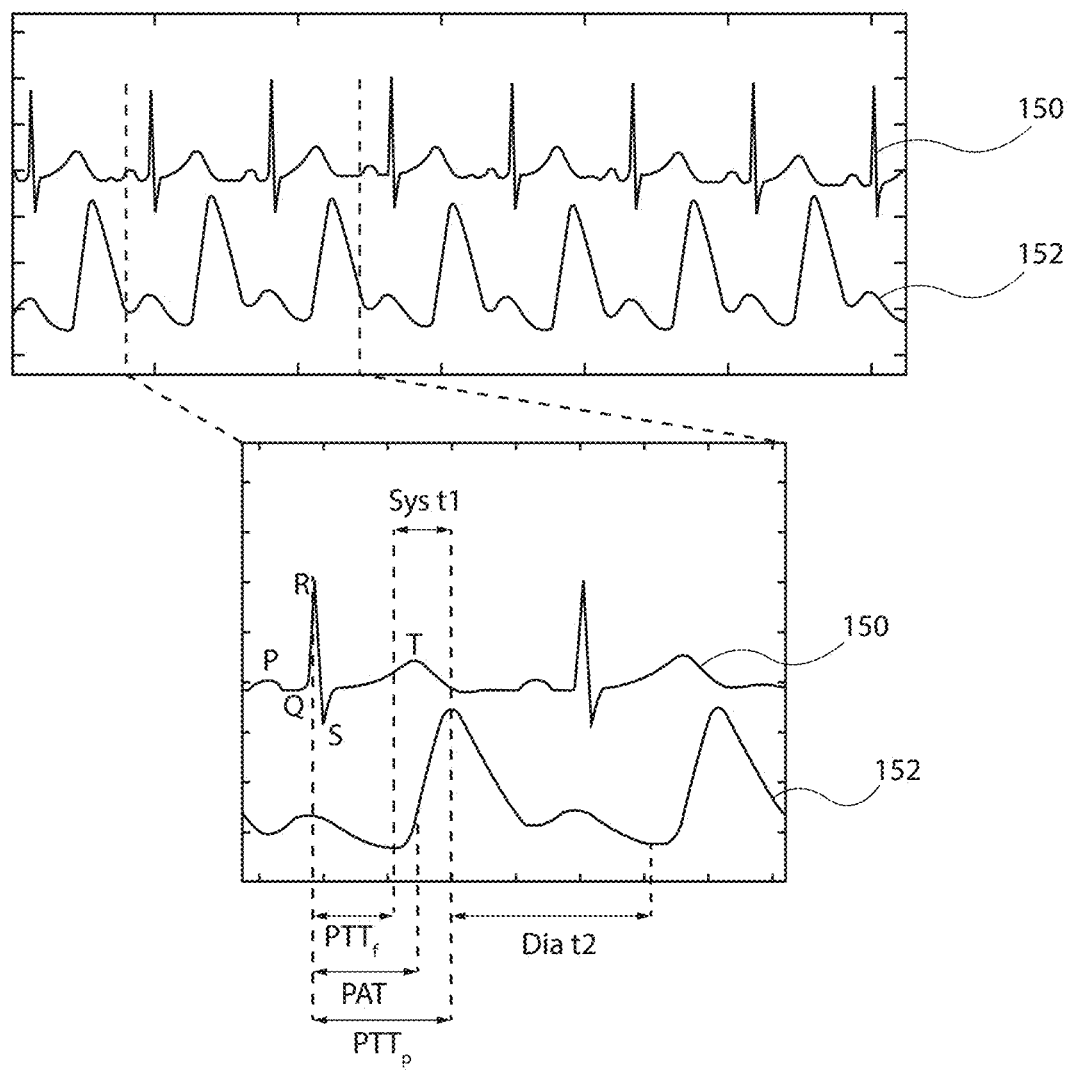
FIG. 15 illustrates a method of measuring $PTT_f$, PAT, $PTT_p$, Sys t1 and Dia t2 using an electrocardiogram signal and a pulse wave signal.
Figure 16:
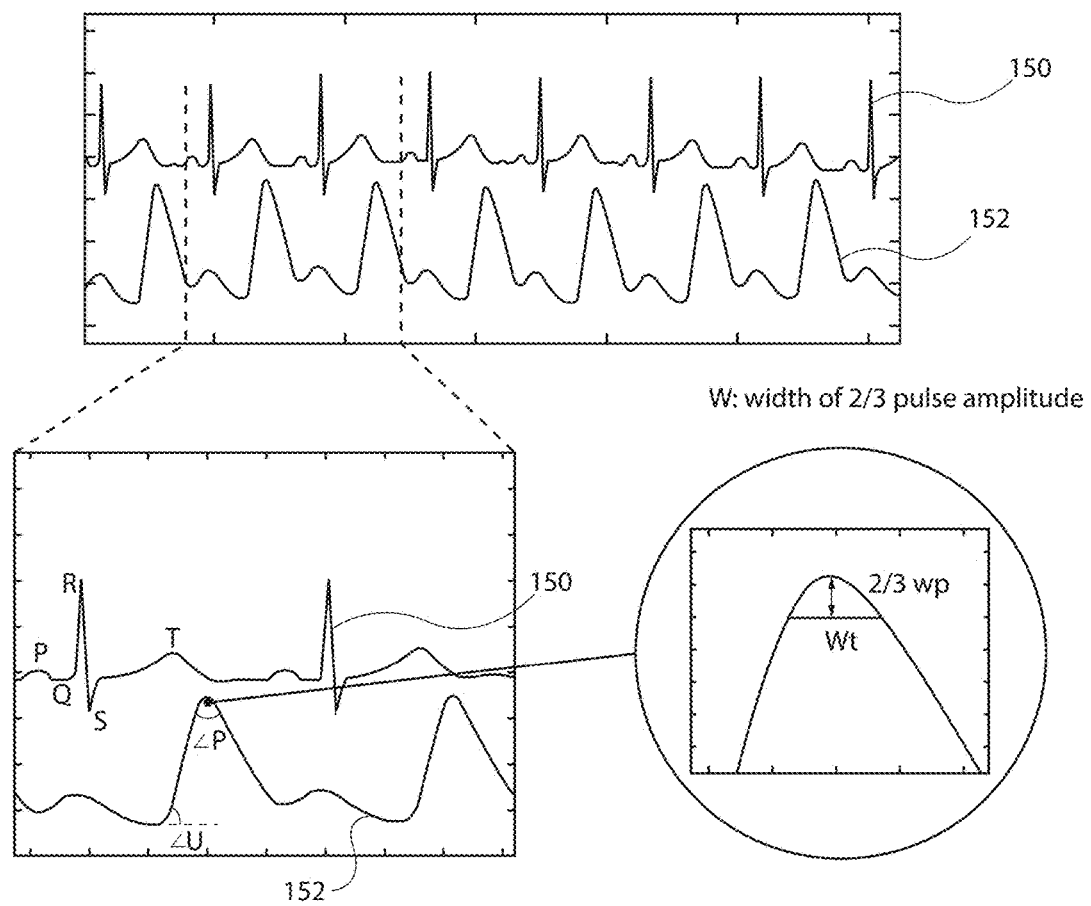
FIG. 16 illustrates a method of measuring $\angle U$, $\angle P$, Wt and W/T using a pulse wave signal.

FIGS. 15 and 16 illustrate readings from a physiological measuring device of some embodiments, in which blood pressure is measured using an electrocardiogram signal 150 and a pulse wave signal 152. In some embodiments, these parameters are derived from a combination of electrocardiogram signals and pulse wave signals. The electrocardiogram signal 150 may describe a QRS complex. The parameters may include the travel time from an R peak of the electrocardiogram signal 150 to a valley point of the pulse wave signal ($PTT_f$), the travel time to a maximum slope point of a pulse wave signal (pulse arrival time or "PAT"), and time to a peak point of a pulse wave signal ($PTT_p$). Some parameters, such as the time from a valley to a peak (Sys t1) and a time from a peak to a next valley (Dia t2) are acquired from only the pulse wave signal 152. Angular parameters, such as $\angle U$ and $\angle P$ may be calculated from a valley angle and a peak angle of a pulse wave signal, respectively. Time parameter Wt may be a time parameter of marked points of a ⅔ amplitude peak. These parameters may be representative characteristics of blood pressure.

Comparing the above parameters in a serial experimental calculation with row-data from a Multiparameter Intelligent Monitoring in Intensive Care (MIMIC) database, the correlations can be obtained to certify that those parameters correlate to blood pressure. The PAT and $PTT_p$ parameters both highly correlate with blood pressure.

Figure 17:
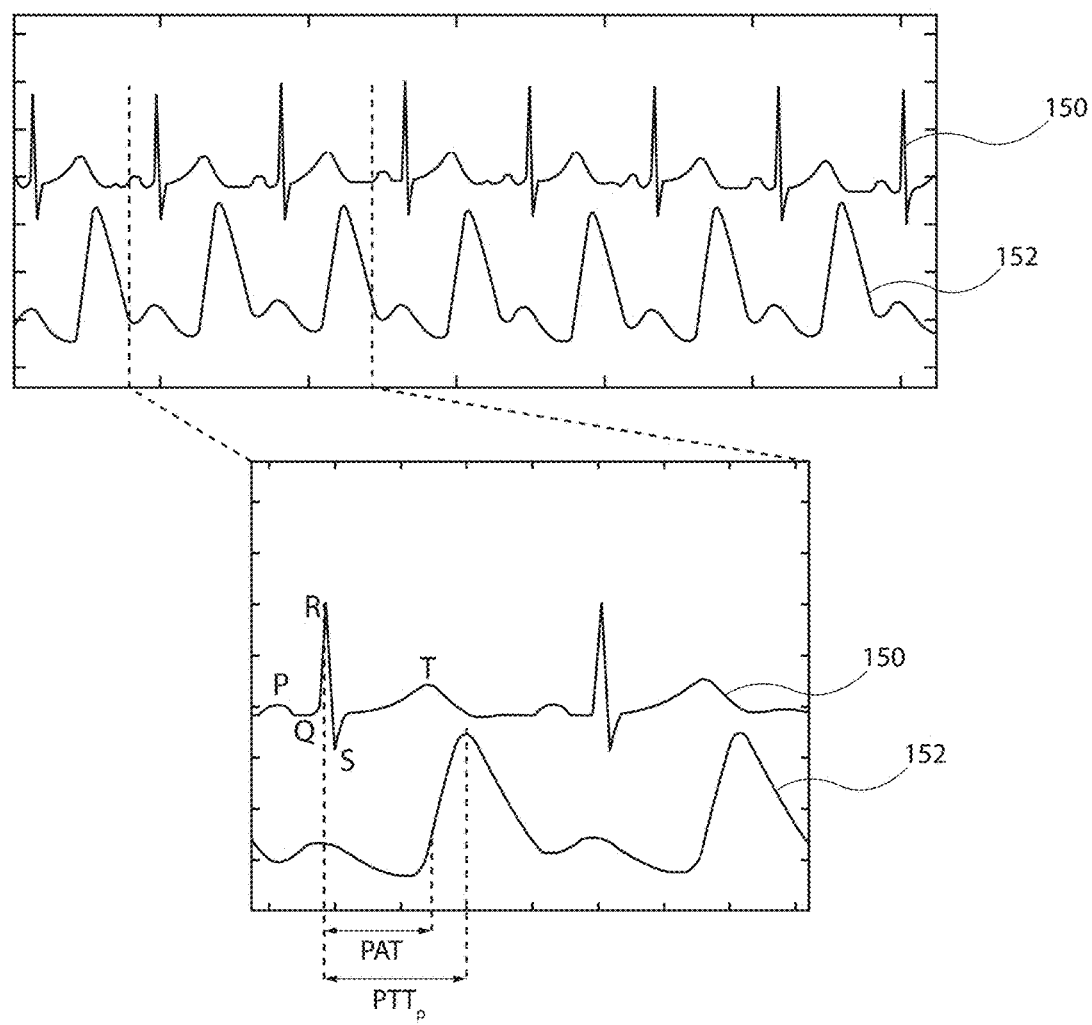
FIG. 17 illustrates a method of measuring PTT utilizing an electrocardiogram signal and a pulse wave signal.

FIG. 17 illustrates a method of measuring a PTT using an electrocardiogram signal 150 and a pulse wave signal 152. The PTT may be a difference in time between an R peak of the electrocardiogram signal 150 and at least two characteristic points of the pulse wave signal 152 measured from, for example, bilateral fingers that are in contact with electrodes and a photo sensor. The PAT and $PTT_p$ may be defined as a time delay of blood traveling from the heart to peripheral arterial sites such as a finger. In particular, the PAT and $PTT_p$ may be calculated using a difference in propagation time between an R peak of an electrocardiogram and a maximum slope point of a pulse wave, and the peak occurrence of a pulse wave, respectively.

The pulse wave velocity (PWV) may be written in the form of Equation (1):

$$PWV = \sqrt{\frac{Eh}{\rho d}} \tag{1}$$

In Equation (1), h denotes the thickness of vessel wall, p denotes the density of blood, d denotes the interior diameter of the vessel, and E denotes the elasticity of the arterial wall (the Young's modulus of a blood vessel).

E may be expressed by Equation (2):

$$E = E_0 \exp^{\alpha P} \tag{2}$$

In Equation (2), $E_0$ is the modulus of the zero pressure, $\alpha$ is a constant that depends on the vessel and may vary from about 0.016 $mmHg^{-1}$ to 0.018 $mmHg^{-1}$. P is the internal blood pressure.

According to Equation (1) and Equation (2), the PWV can be rewritten as Equation (3):

$$PWV = \sqrt{\frac{hE_0 e^{\alpha P}}{\rho d}} \tag{3}$$

In Equation (3), the PWV may vary based on blood pressure, blood vessel diameter, blood viscosity and blood vessel thickness. For example, the PWV may become faster as a blood vessel is thicker. Furthermore, as the elasticity of blood vessel decreases, the PWV becomes faster. As an arterial index, PWV may be of interest for patients at risk for or having hypertension, arteriosclerosis, peripheral arterial occlusion, kidney ailments, or other conditions.

In another aspect, the PWV may be calculated by dividing, by PAT, the length of a blood vessel, L. Therefore, the PAT can be expressed by Equation (4), which is based on Equation (3).

$$PAT = \frac{L}{PWV} = L\sqrt{\frac{\rho d}{E_0 h}} e^{-\frac{\alpha}{2}P} \tag{4}$$

In Equation (4), P is blood pressure. L may be calculated by actually measuring the length of the blood vessel or based on a regression equation using the gender and height of the user. Examples of regression equations are Equation (5) and Equation (6), but the regression equation used in the embodiments described herein is not restricted thereto.

$$L = 0.745 \times (\text{Height} - 53.4)(\text{cm}) \tag{5}$$

$$L = 1.015 \times (\text{Height} - 81.0)(\text{cm}) \tag{6}$$

Equation (5) and Equation (6) represent regression equations of half arm-span with regard to an Asian male and female, respectively, and indicate a length from the heart to his or her finger.

Furthermore, another way to investigate the length of the user's arm span is to calculate velocity versus arm-length through adaptation of the sensor unit. In particular, the length L may be approximately measured based on the velocity of the movement of a user's straight arm. The velocity is dependent on the rate at which the arm moves from a steady situation to spin about the user's shoulder. The velocity can be determined based on acceleration and time. The distance traveled by the arm in one rotation is given by the circumference, $2\pi L$, which can be calculated by relations between velocity and time to calculate the length of the arm L. Various movement sensors in the apparatus may be used to measure one or more characteristics of this movement in order to estimate the length of the user's arm. The apparatus may be configured to provide instructions to the user regarding how to move in a manner to produce accurate calculations.

The blood pressure may be calculated by Equation (5) or Equation (6), based on the length L and a PAT calculated based on the electrocardiogram signal and a pulse wave signal. Thus, a PWV value may be calculated by substituting a length of the blood vessel L and a PTT in Equation (4).

Figure 19:
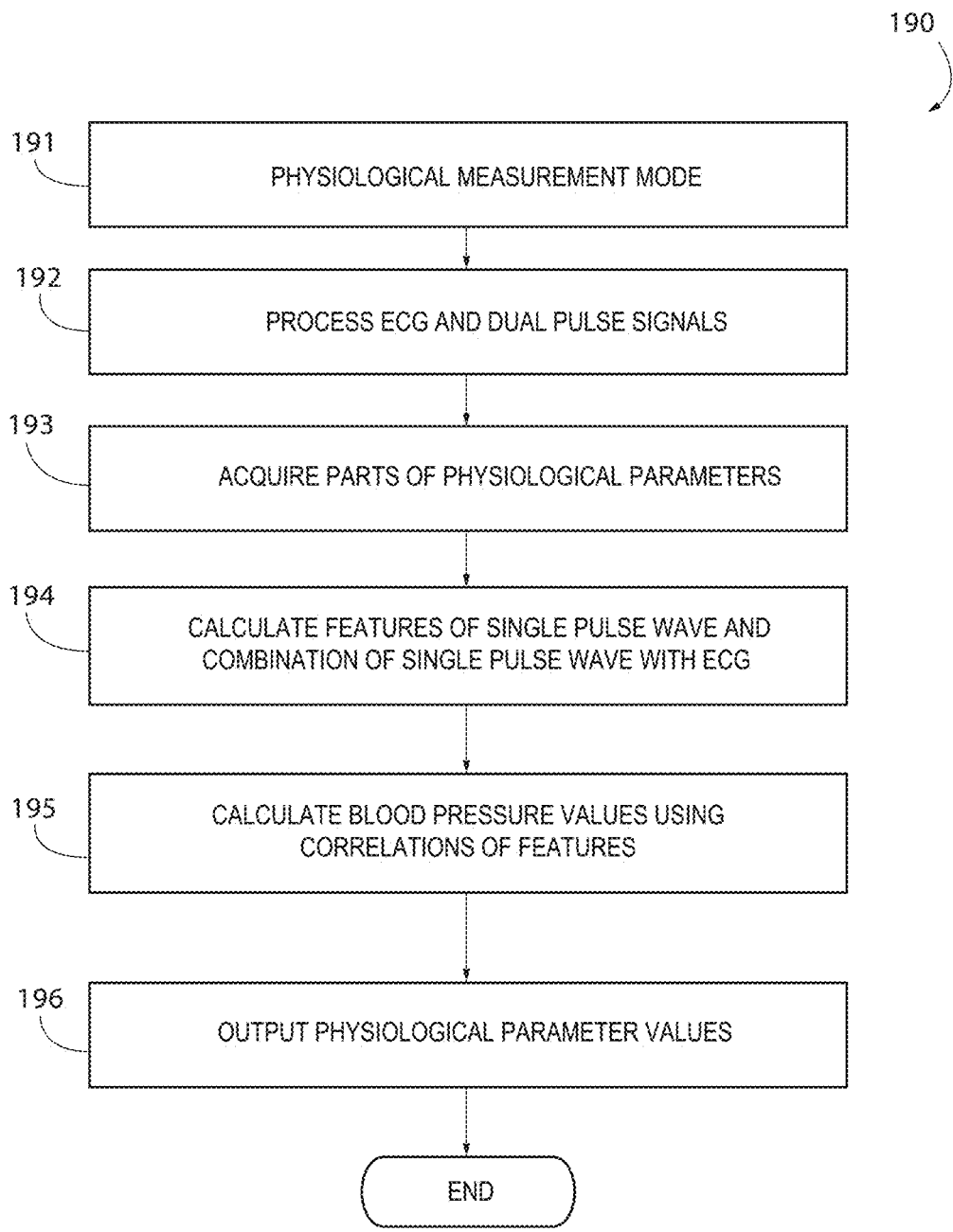
FIG. 19 illustrates operations of a portable terminal in accordance with an embodiment.

Referring to FIG. 19, when a PAT and a PWV are calculated, the blood pressure value is calculated by substituting a PTT and a PWV in Equation (4). The blood pressure value denotes the average blood pressure P in Equation (4).

In another aspect, since more parameters have higher correlation with blood pressure such as PAT and $PTT_p$, the systolic blood pressure and diastolic blood pressure may be established based on the regression parameters PAT, $PTT_p$ and heart rate (HR). The Equations are as follows.

$$\text{Systolic} = c_1 + \alpha_1 PAT + \beta_1 PTT_p + \gamma_1 HR \tag{7}$$

$$\text{Diatolic} = c_2 + \alpha_2 PAT + \beta_2 PTT_p + \gamma_2 HR \tag{8}$$

Equation (7) and Equation (8) show estimation models used to determine the systolic and diastolic blood pressures, respectively, where $c_1$, $\alpha$, $\beta$, and $\gamma$ are parameters to be calibrated for each user.

The systolic blood pressure and diastolic blood pressure may be calculated simultaneously using Equation (7) and Equation (8) when $PTT_p$ and heart rate are calculated and PAT is based on an electrocardiogram signal and a pulse wave signal. Furthermore, the physiological measurement not only may be used to calculate blood pressure values but may also be evaluate the elasticity of blood vessel based on a PWV.

Figure 18:
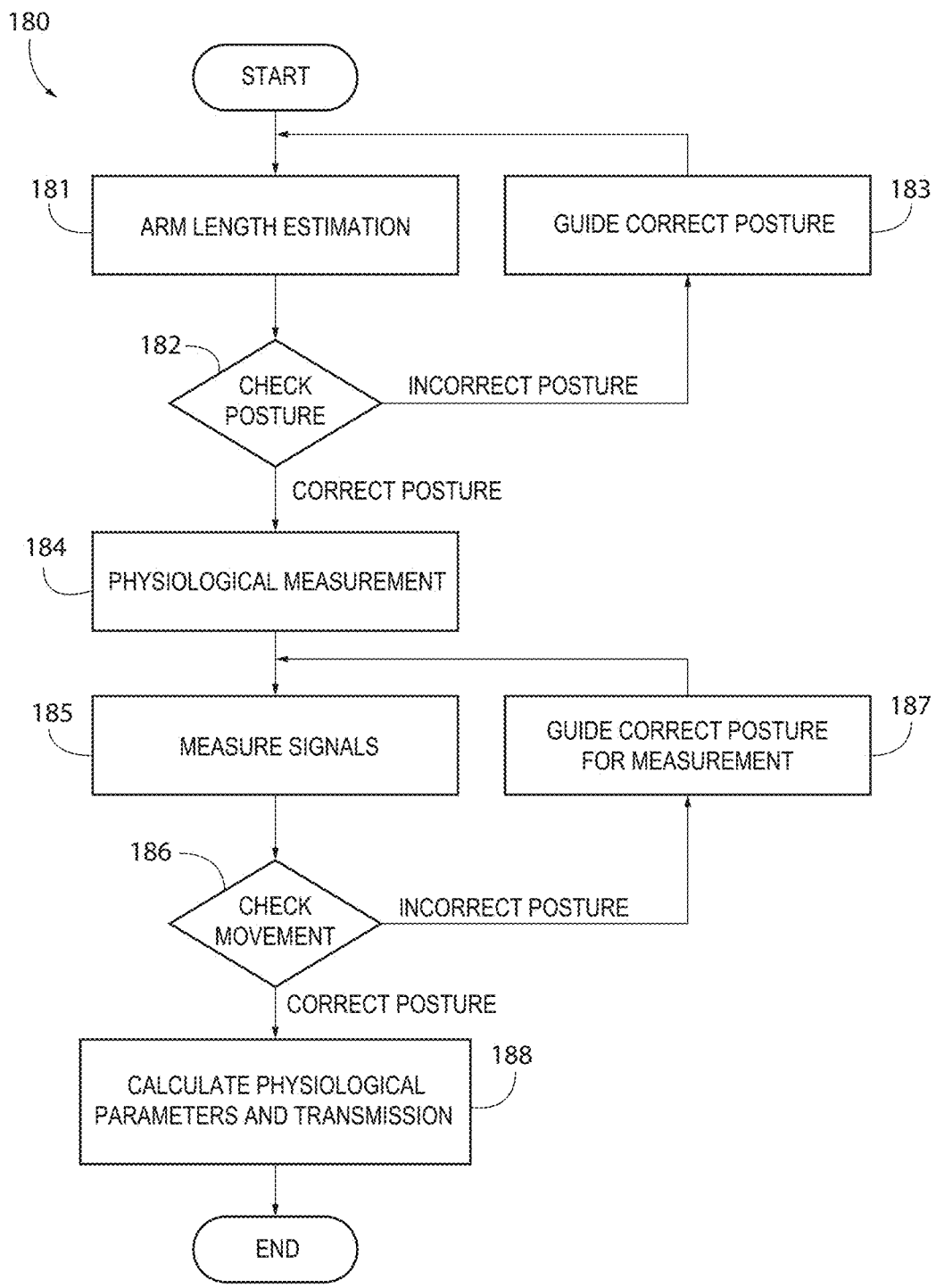
FIG. 18 illustrates operations of a portable physiological measuring apparatus in accordance with an embodiment.

FIG. 18 is a flow diagram illustrating a method 180 for measuring one or more physiological parameters using a portable physiological measuring apparatus, according to an embodiment. According to FIG. 18, the portable physiological measuring apparatus 1 starts to estimate an arm's length of a user in step 181. In step 182 (which may occur during step 181), the apparatus determines whether the user has correct or incorrect posture. Incorrect posture may lead to inaccurate results. The signal processing unit 6 of the portable physiological measuring apparatus 1 may calculate the length of the blood vessel by measuring the distance from a heart to the pulse wave signal measuring point based on the signal received from the second sensor unit 5. In this example, a proper operating track posture of the portable physiological measuring apparatus 1 in estimating the arm's length may be defined in advance. When the user's posture is incorrect (e.g., if the user's arm is bent during the estimation of the arm's length), a correct posture for use is guided in step 183 so that the apparatus may estimate the arm's length in a proper posture. For example, the apparatus may guide the user into correct posture by providing audio or visual cues to the user.

If it is determined that the user does have a correct posture while the arm's length is measured, a movement signal (such as a signal from a tri-axial accelerometer) may be transmitted to the signal processing unit 6 for estimation of the arm length. The portable physiological measuring apparatus 1 may proceed with a physiological measurement in step 184 by measuring an electrocardiogram signal, dual pulse wave signals, and a body temperature value in step 185 when the user presses on the appropriate area of the device (e.g., on the electrocardiogram circuit unit 2, the pulse circuit unit 3, the first sensor unit 4 and the second sensor unit 5). During measuring, step 186 determines whether the user is moving. For example, the signal processing unit 6 of the portable physiological measuring apparatus 1 calculates a movement value associated with a degree of the tilt or a distance of the movement based on a signal received from the second sensor unit 5. In this example, a threshold value may be set in advance for determining whether the portable physiological measuring apparatus 1 is tilted or the user is in motion. The threshold value may be adjusted by improving accuracy of the portable physiological measuring apparatus 1.

When the calculated movement value is greater than the threshold value (e.g., when the degree of the tilt is greater than or equal to an angle or the user is in motion), a correct posture for use is guided in step 187, so the user may measure physiological signals in a correct posture. When the portable physiological measuring apparatus 1 is tilted or the user is in motion, it is hard to obtain an accurate measured physiological value including in a blood pressure value, SpO2, heart rate, and body temperature, and thus, a measured electrocardiogram signal, dual pulse wave signals and a body temperature value may not be calculated through the signal processing unit 6 and transmitted to the portable terminal 10.

When it is determined that movement of the portable physiological measuring apparatus 1 is below a threshold, the apparatus may measure an electrocardiogram signal, dual pulse wave signal, and a body temperature value. In step 188, the portable physiological measuring apparatus 1 may transmit to a portable terminal, or calculate for itself, the measured electrocardiogram signal, dual pulse wave signal, and a body temperature value.

FIG. 19 is another flow diagram illustrating a method 190 for measuring one or more physiological parameters using a portable physiological measuring apparatus, according to an embodiment. The operations may be performed by a portable terminal (e.g., portable terminal 10), on the physiological measurement apparatus itself, or elsewhere. The process begins in a physiological measurement mode step 191, such as when a physiological measurement application is executed. In step 192, the electrocardiogram signal, dual pulse wave signals and a body temperature value are processed. The physiological parameters, such as SpO2, heart rate and a body temperature are acquired in step 193 (e.g., from the portable physiological measuring apparatus 1 if the process is executed on a portable terminal 10). Next, features of a pulse wave and combination of a pulse wave, and an electrocardiogram are calculated in step 196. With the calculation of these features, blood pressure values may be calculated based on correlations of these features in step 195. When a physiological parameter value is calculated, such as but not limited to blood pressure, SpO2, heart rate, and body temperature, the physiological parameter values may be displayed or otherwise outputted, as in step 196.

Figure 20A:
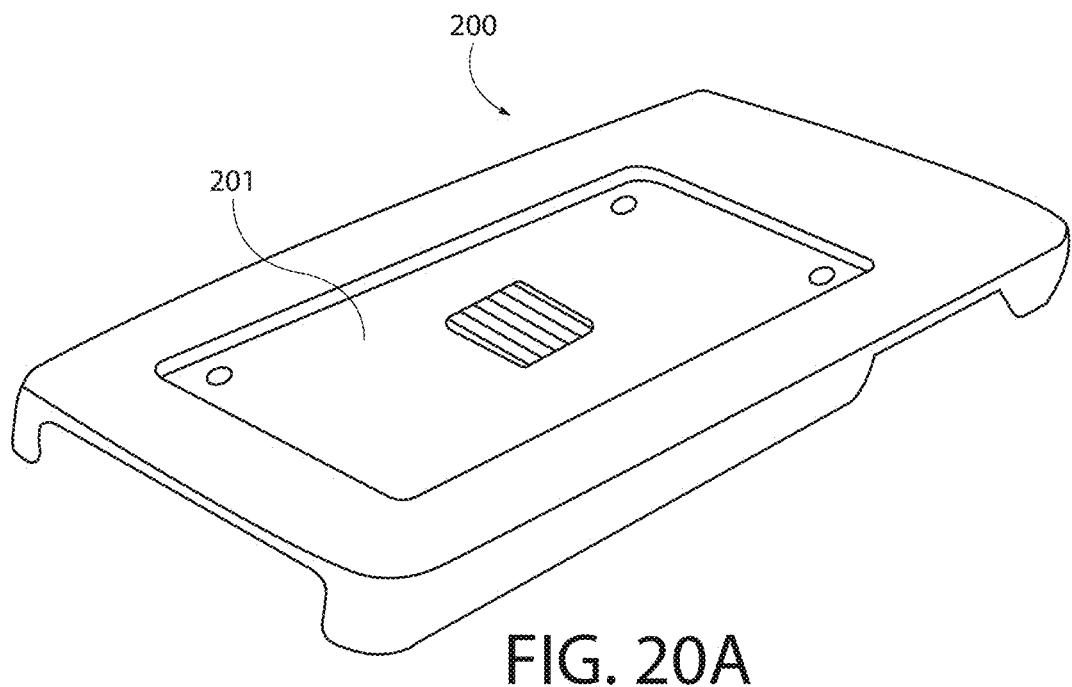
FIG. 20A illustrates a perspective view of an embodiment of a mobile device case having a device slot.

FIG. 20A illustrates a perspective view of an embodiment of a mobile device case 200 having a device slot 201. The mobile device case 200 may be a case or other covering for a mobile device. The case 200 may provide protection to the device, decoration of the device, or other benefits to the device. The case 200 may be integrated with the mobile device during manufacturing and/or may be an aftermarket consumer good that may clip on or otherwise attach to a mobile device. The device slot 201 may be sized and shaped to receive and retain a measurement apparatus 202. In this manner, a user may conveniently carry the apparatus with a mobile device.

Figure 20B:
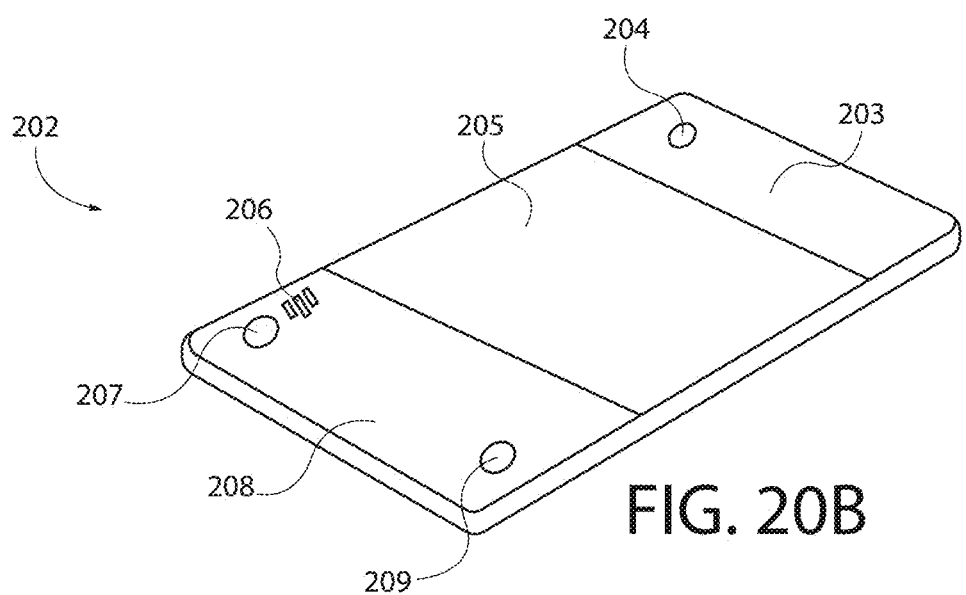
FIG. 20B illustrates a perspective view of a device configured to fit within the device slot of the embodiment of FIG. 20A.

FIG. 20B illustrates a perspective view of a measurement apparatus 202 configured to fit within the device slot 201 of the mobile device case 200 of FIG. 20A. In particular, the measurement apparatus includes a sensor 203, a button 204, a display 205, an SpO2 sensor 206, a button 207, a sensor 208, and a button 209. The measurement apparatus 202 may be constructed according to the various embodiments described herein. For example, the sensors 203 and 208 may be electrodes or other sensors for receiving information. The buttons 204, 207, and 209 may be physical or virtual buttons with which a user may operate the measurement apparatus 202. The display may be an interface through which a user may receive information. The SpO2 sensor 206 may be a sensor for detecting blood oxygen levels.

Figure 21A:
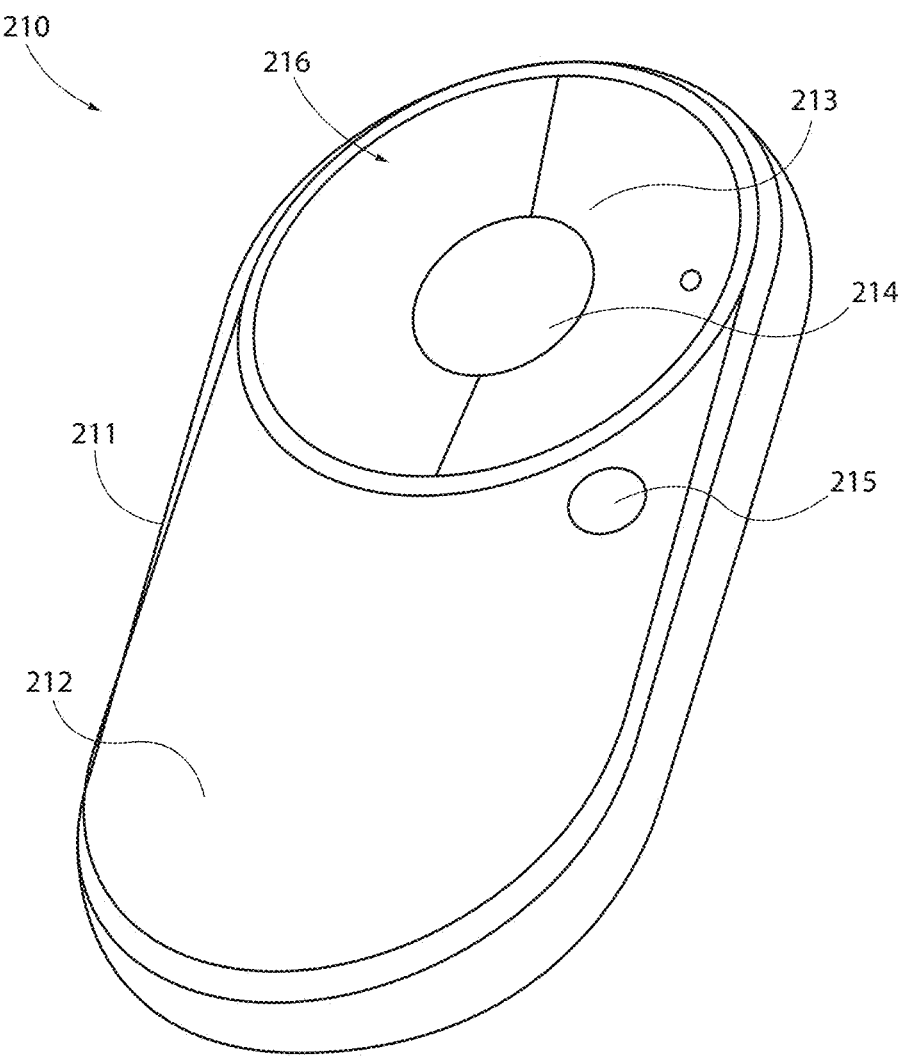
FIG. 21A illustrates a perspective view of an embodiment of a portable blood pressure monitoring apparatus.

FIG. 21A is a perspective view of another embodiment of a portable blood pressure monitoring apparatus 210. In this embodiment, the apparatus 210 includes a housing 211 with an indented portion 216 at one end of its top surface 212. In some embodiments, the indented portion 216 or a portion thereof is formed from an electrodconductive material that acts as a first electrode 213. In other embodiments, the first electrode 213 is located at the bottom of indented portion 216. The indented portion 216 includes one or more sensors 214 located at the bottom of the indented portion 216. In some embodiments, the sensor 214 may be located inside the first electrode 213 at the bottom of the indented portion 216. The top surface 212 itself, outside of the indented portion 216, is made of an electroconductive material and acts as a second electrode. In embodiments where both the indented portion 216 and the top surface 212 act as electrodes, the two portions may be electrically isolated from each other using, for example, an insulating spacer separating the portions. The shape of indented portion 216 may facilitate the proper placement of a thumb, finger, or other body part on the first electrode 213 and the sensor 214. The sensor 214 may be a single sensor or a cluster of multiple sensors. The thumb or a finger of the other hand of the user may be placed on the top surface 212 away from the indented portion 216, to enable measurement of an electrocardiogram signal of the user. The button 215 may be used to turn the apparatus 210 on and off and/or to control one or more features of the apparatus.

The apparatus 210 may have various shapes and sizes. In some embodiments, the apparatus 210 may be relatively small and thin, for example smaller and thinner than a typical smart phone. For example, in various embodiments, the apparatus 210 may have a length of about 60 mm to about 80 mm, and in one embodiment it may have a length of about 72.02 mm. The apparatus 210 may have a width of about 20 mm to about 40 mm, and in one embodiment it may have a width of about 36.02 mm. The apparatus 210 may have a thickness of about 5 mm to about 9 mm, and in one embodiment it may have a thickness of about 7.05 mm. The indented portion 216 may be circular and have a diameter of about 25 mm to about 35 mm, and in one embodiment it may have a diameter of about 32.2 mm. These are only exemplary dimensions provided for illustrative purposes.

Figure 21B:
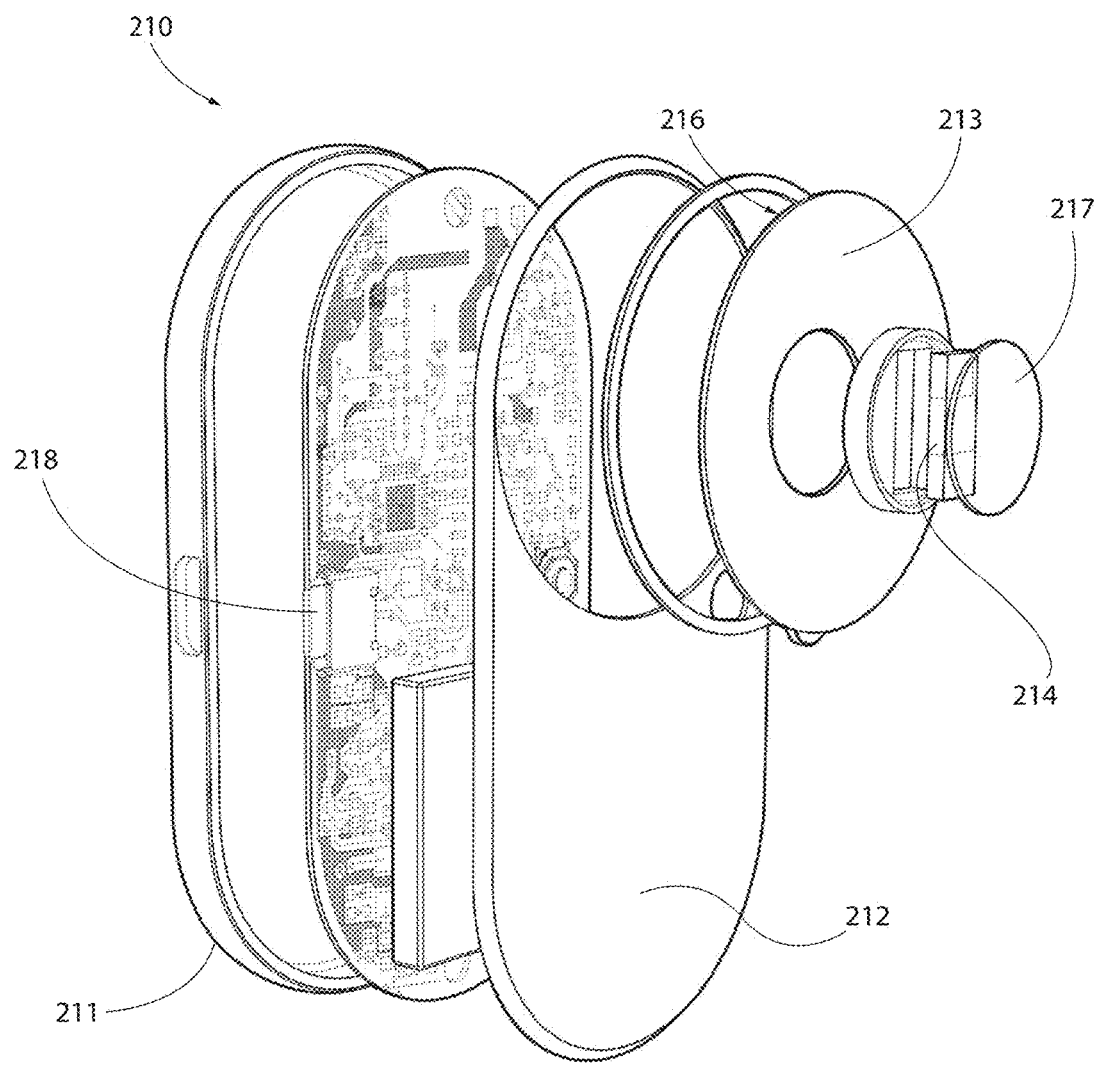
FIG. 21B illustrates an exploded perspective view of the embodiment of the portable blood pressure monitoring apparatus of FIG. 21A.

FIG. 21B is an exploded perspective view of the apparatus 210 of FIG. 21A. The one or more sensors 214 may be located behind or incorporated with a protective covering 217. The apparatus 210 may further comprise a port 218, which may facilitate charging the apparatus 210, powering the apparatus 210, syncing data, and other actions.

Figure 22:
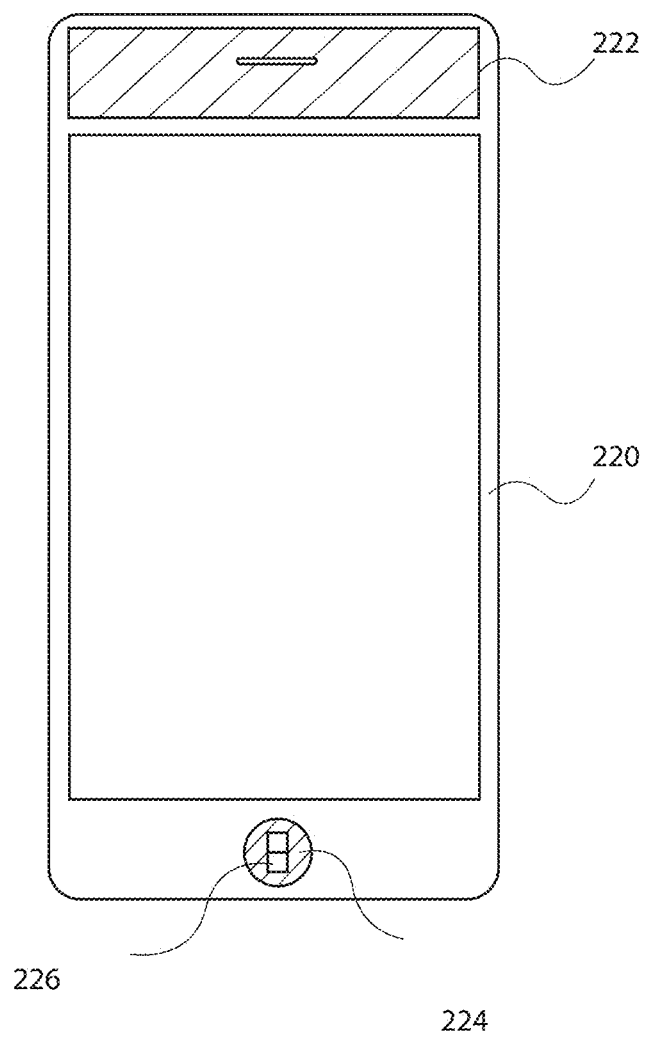
FIG. 22 illustrates perspective view of an embodiment of a portable blood pressure measuring apparatus using a smart phone in a case.

FIG. 22 illustrates a perspective view of an embodiment of a portable blood pressure measuring apparatus integrated into a mobile phone 220 and/or a case thereof. The apparatus includes a first electrode 222 and a second electrode 224 having negative and positive poles in a surface of a body, and an optical sensor 226. The optical sensor 226 may be in the same or substantially the same position as the second electrode 224. In an embodiment, the first electrode 222, the second electrode 224, and the optical sensor 226 are integrated with the mobile phone 220. In another embodiment, the second electrode 224 and the optical sensor 226 are integrated in a home or other button of the mobile phone 220. The first electrode 222 surrounds or is located near an earpiece area of the mobile phone 220 that is contacted to a user's ear when the user uses the mobile phone 220 to make a phone call. Another embodiment may be configured such that when the user brings a finger from the user's right hand into contact with the first electrode 222, and brings another finger from the left hand into contact with the second electrode 224, the apparatus may simultaneously measure an ECG signal and/or a photoplethysmogram signal for measuring blood pressure, pulse oximetry and heart rate.

Figure 23A:
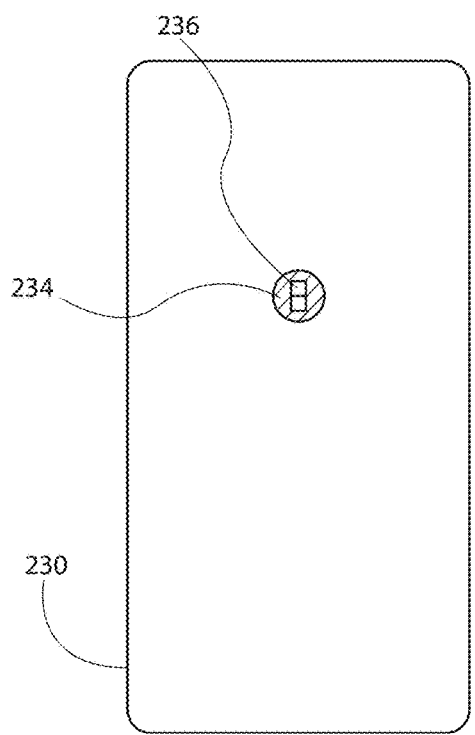
FIG. 23A illustrates a rear view of an embodiment of a portable blood pressure measuring apparatus using a smart phone.
Figure 23B:
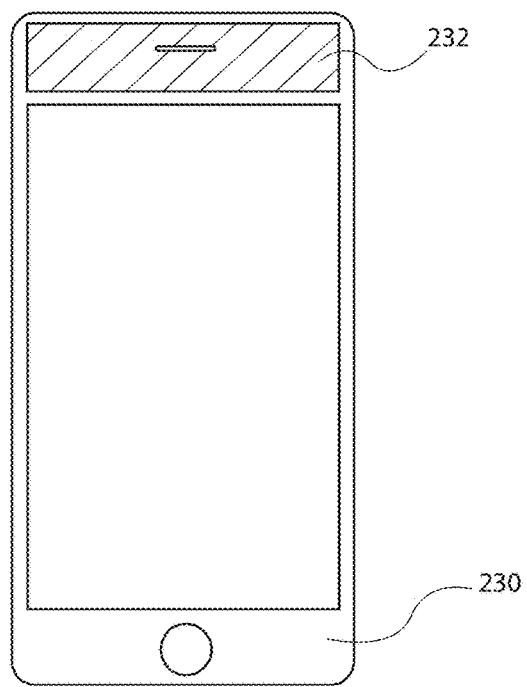
FIG. 23B illustrates a front view of the embodiment of FIG. 23A.

FIG. 23A illustrates a front view of an embodiment of a portable blood pressure measuring apparatus that includes a smart phone in a case in accordance with an embodiment. FIG. 23B illustrates a back view of the portable blood pressure measuring apparatus 1 of FIG. 23A. As illustrated, a mobile phone 230 may include a first electrode 232, a second electrode 234, and an optical sensor 236. The optical sensor 236 may be in the same position as the second electrode 234. In this embodiment, the first electrode 232, the second electrode 234, and the optical sensor 236 are integrated with the mobile phone 230. In an embodiment, the first electrode 232 surrounds or is located near an earpiece area of the mobile phone 230 and the second electrode 234 and the optical sensor 236 are located on the back of the mobile phone 230.

Figure 24:
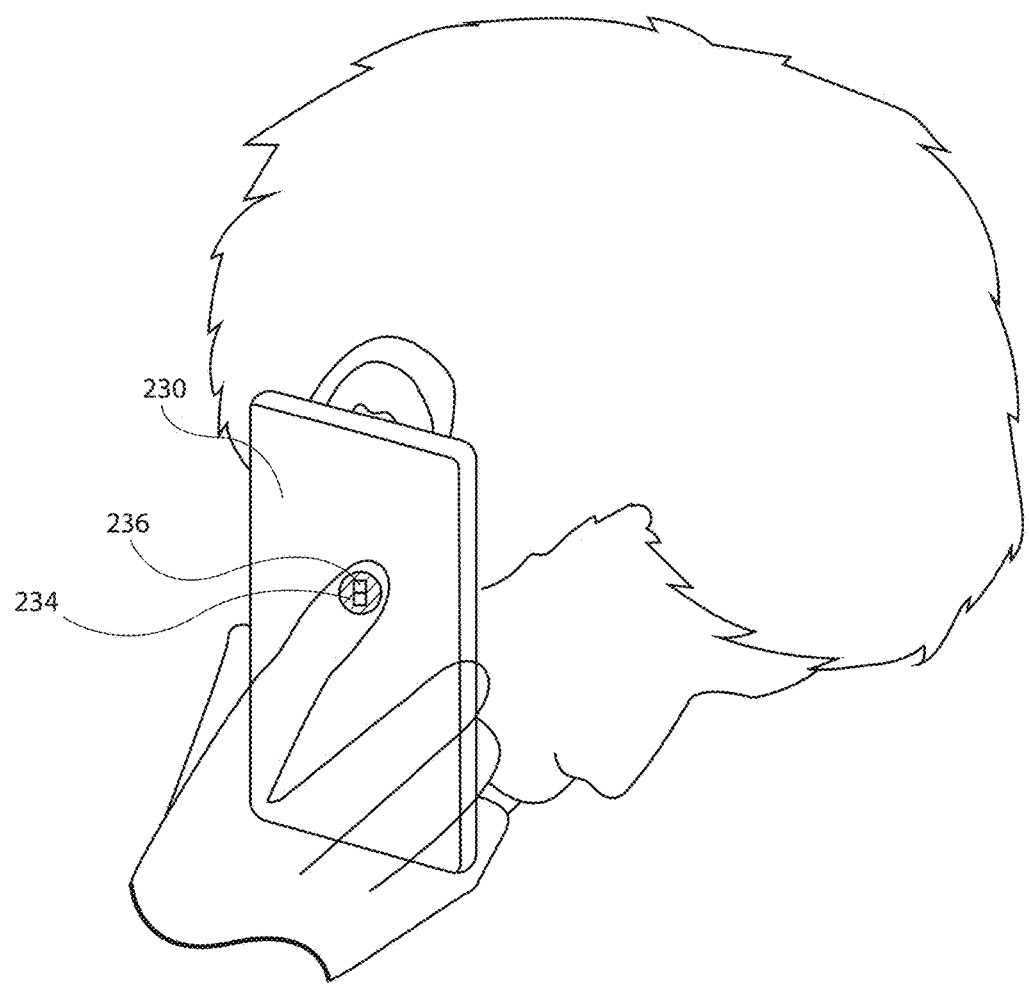
FIG. 24 illustrates a user taking physiological measurements using an embodiment of a mobile device that performs mobile cardiovascular monitoring.

FIG. 24 illustrates a user taking physiological measurements while holding the portable blood pressure measuring apparatus of FIG. 23A against the user's ear. In particular, FIG. 24 provides a view illustrating how to simultaneously measure ECG and pulse wave using a mobile phone 230. The mobile phone 230 may include a first electrode 232, a second electrode 234 and an optical sensor 236. This embodiment may be used to measure physiological signs while a user is using the mobile phone to talk by contacting the first electrode 232 with an ear and putting a finger into contact with the second electrode 234 and optical sensor 236. The measured results may be stored in the mobile phone 230 and the user may check the results using a display of the mobile phone 230.

Figure 25:
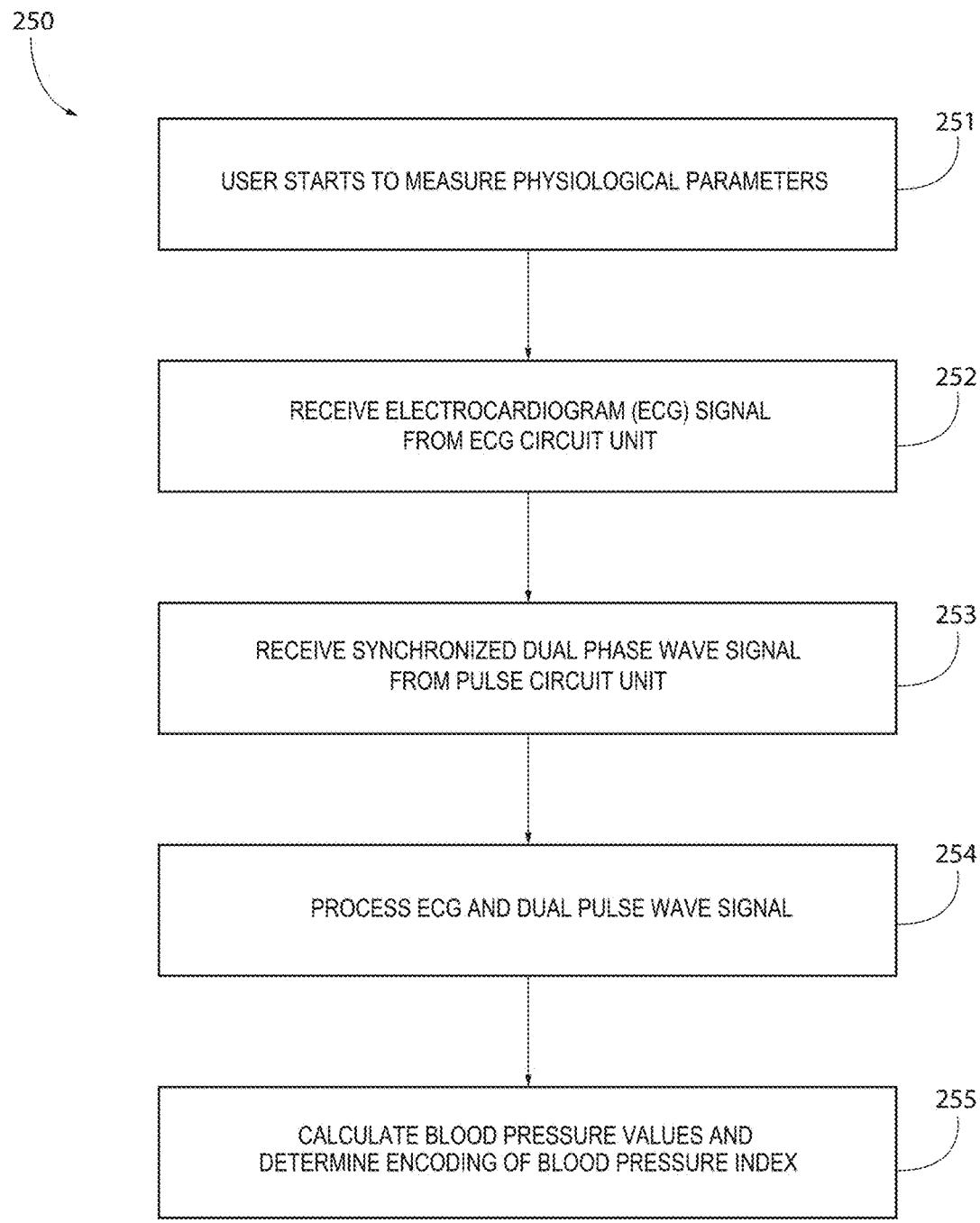
FIG. 25 is an exemplary chart illustrating steps that may be performed as described herein.

FIG. 25 illustrates a method of using a portable physiological measuring apparatus according to an embodiment. In particular, a user may begin to measure physiological parameters in step 251. This step may include making physical contact with the electrocardiogram circuit unit 2 and the pulse circuit unit 3. In step 252, the apparatus may receive an electrocardiogram signal from the electrocardiogram circuit unit 2 over a period of time. In an embodiment, a dual pulse wave signal may also be received during this same period of time 253 from the pulse circuit unit 3. The electrocardiogram signal and the dual pulse wave signal may then be processed 254 by the signal processing unit 6 of the portable physiological measuring apparatus 1 or the portable terminal 10. Some parameters of the electrocardiogram signal and the dual pulse wave signal may be determined and used to calculate blood pressure values. Through the blood pressure index encoding process, the state of the user's blood pressure may be clearly described and displayed in step 255.

Figure 26:
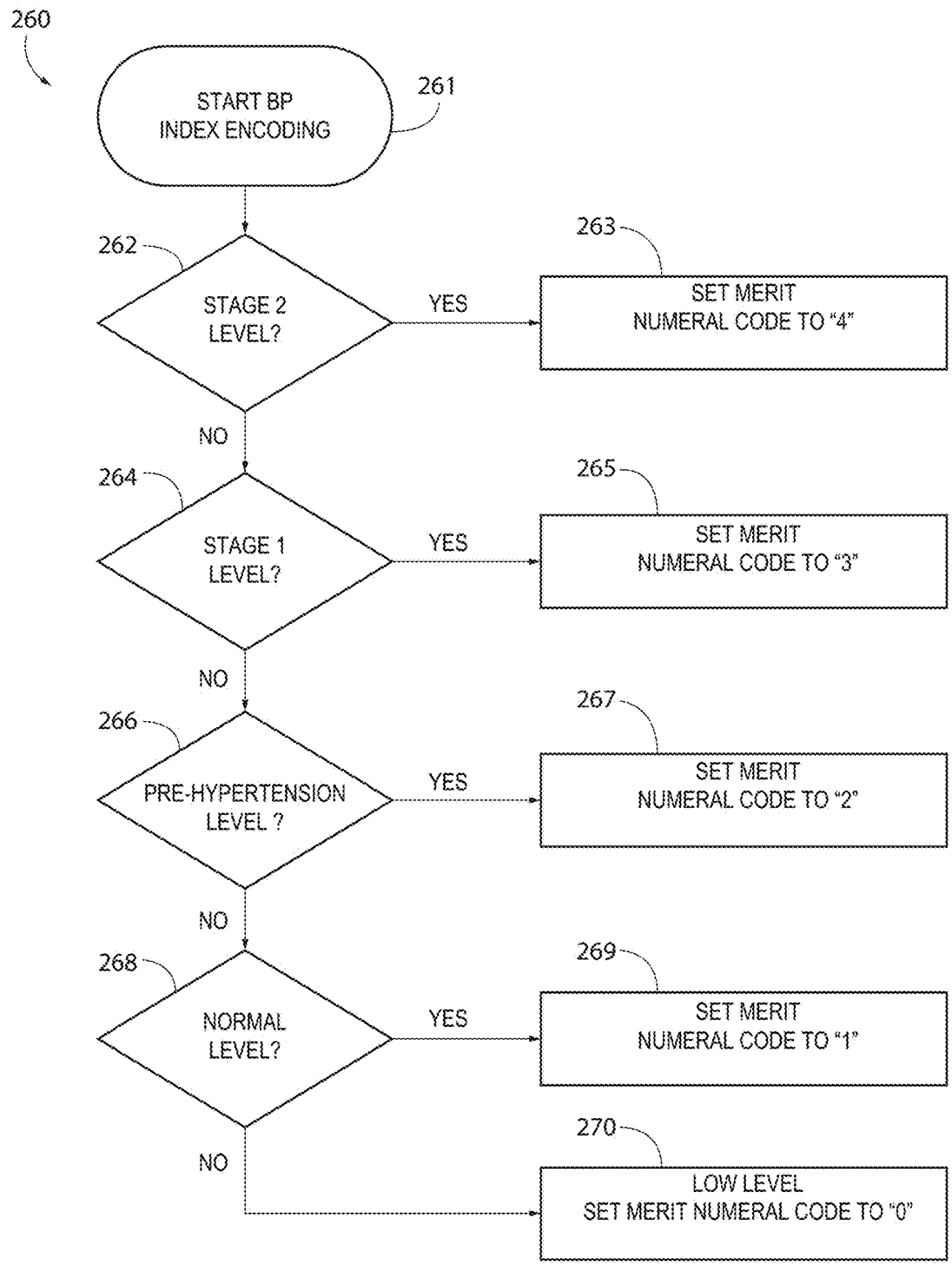
FIG. 26 illustrates the process by which the results of the blood pressure index analysis are encoded into the numeral code.

FIG. 26 illustrates a process by which the results of the blood pressure index analysis are encoded into a blood pressure index, which may include a numerical code. The rectangles indicate task or action blocks (e.g. actions blocks designated 263, 265, 267, 269, and 270). The diamonds indicate decision blocks (e.g. decision blocks 261, 262, 264, 266, and 268) with the answer to the enclosed question determining which path to take next.

Determining whether a user is in stage 2 in step 262 may include determining whether both: (a) the user's systolic blood pressure (SBP) is less than or equal to 160 mmHg and (b) the user's diastolic blood pressure (DBP) is less than or equal to 100 mmHg. If so, then the numeral code of the blood pressure index may be set to "4" in step 263. Determining whether a user is in stage 1 in step 264 may include determining if: (a) 140≤SBP<160 and DBP<90 mmHg; or (b) 140≤SBP<160 and 90≤DBP<100 mmHg; or (c) SBP<140 and 90≤DBP<100 mmHg. If so, then the numeral code of the blood pressure index may be set to "3" in step 265. Determining whether a user is in a pre-hypertension level in step 266 may include determining if: (a) 120≤SBP<140 and DBP<80 mmHg; or (b) 120≤SBP<140 and 80≤DBP<90 mmHg; or (c) SBP<120 and 80≤DBP<90 mmHg. If so, then the numeral code of the blood pressure index may be set to "2" in step 267. Determining whether a user is at a normal level in step 268 may include determining if (a) 90≤SBP<120 and DBP≤60 mmHg; or (b) 90≤SBP<120 and 60≤DBP<80 mmHg; or (c) SBP<90 and 60≤DBP<80 mmHg. If so, then the numeral code of the blood pressure may be set to "1" in step 269. If SBP<90 mmHg and DBP<60 mmHg, then the numeral code may be set to "0" in step 270.

For example, if the user uses the portable physiological measuring apparatus to evaluate his or her cardiovascular status and the blood pressure and determines that his/her blood pressure is 135/75 mmHg, then the numeral code of the index will be set to "2". In another example, if the blood pressure is measured as 148/92 mmHg, then the numeral code will be set to "3". The numeral code may include five levels representing different degrees of cardiovascular condition. The numeral code "0" may represent low blood pressure level, "1" may represent normal blood pressure level, "2" may represent prehypertension level, "3" may represent stage 1 hypertension blood pressure level, and "4" may represent stage 2 hypertension blood pressure level.

Figure 27:
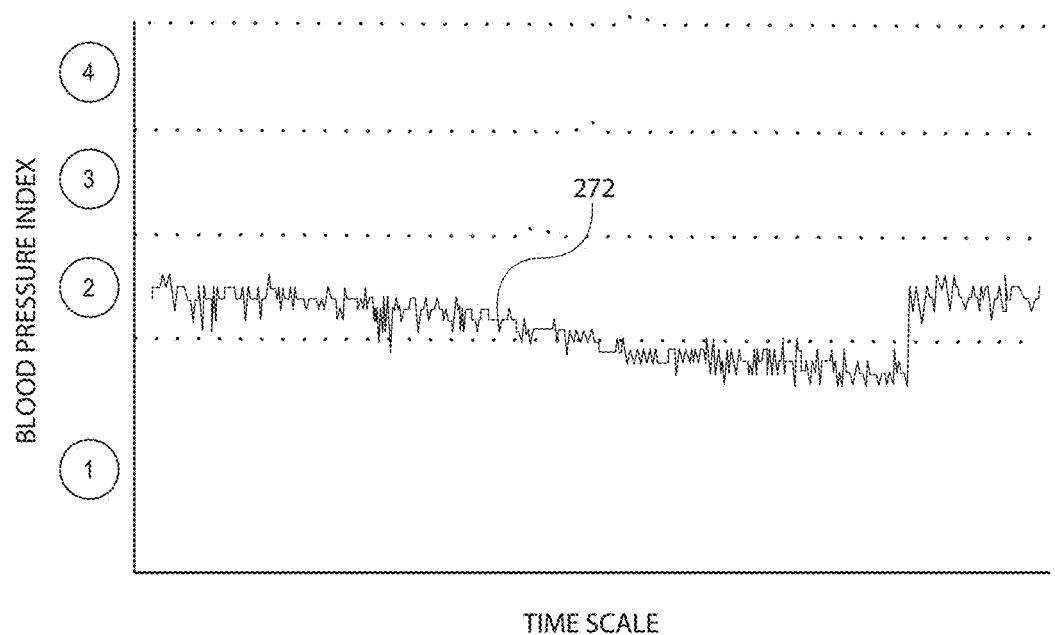
FIG. 27 is a trend chart illustrating blood pressure of a person over time with corresponding to index categories.

FIG. 27 is a trend chart illustrating blood pressure of a person over time with corresponding to index categories. The graph of FIG. 27 illustrates blood pressure index trend waveform 272. The waveform is plotted versus the number of days since measuring. In this example, the blood pressure index is an indicator of cardiovascular status. Although the blood pressure index does not represent true blood pressure, the trend of the blood pressure index over time will be very similar to the trend of the true blood pressure. Therefore, carrying a small physiological measuring apparatus with displayed the blood pressure index helps a user record and analyze the change of the cardiovascular status regularly. Higher blood pressure trajectories are associated with an increased risk of coronary artery calcification. See Allen et al., Blood Pressure Trajectories in Early Adulthood and Subclinical Atherosclerosis in Middle Age, JAMA. 2014; 311(5):490-497 Therefore, if the blood pressure index numeral code shows "2" or gradually increased from "2" to "4" for a long time, then the risk of coronary artery coefficient will be significantly increased. However, to understand the change of the blood pressure index over time and implement the appropriate health management policies will help and improve the cardiovascular health. In an embodiment, if a user's numeral code shows "4" for a long time, excepting assistance from suitable diet and exercise, he or she should cooperate with professional doctors and start medication to control the hypertension effectively.

In sum, the disclosed embodiments include systems and methods for predicting cardiovascular status. The blood pressure index can be displayed and stored conveniently in the portable physiological measuring apparatus 1 and a portable terminal 10.

Map+GPS Display. In some embodiments, the apparatus may include or communicate with a GPS receiver. The apparatus may also be configured to access mapping data. The mapping information and GPS data may be used to show nearby hospitals and/or landmarks for easy recognition by the user. This information may be helpful if the user needs to locate a hospital for assistance. The mapping information and GPS data may also be used to track location data along with measured physiological data to determine whether particular locations are correlated with particular measurements. In addition, the GPS or other positioning data may be sent to emergency personnel or family members of the user in order to facilitate locating the user.

Emergency Button. In some embodiments, the apparatus may include an emergency button. The emergency button may be used to place the user in contact with emergency personnel, summon assistance, or provide other functionality. In embodiments where contact with emergency personnel is automatically made following detection of an emergency (e.g., due to particular physiological readings), the emergency button may be used to confirm the user's consent to make an emergency call. The emergency or other button may be configured to call a predefined emergency contact, thus bypassing the need to search for contacts on a phone.

Patient history and insurance information. The user's patient history may be stored on the device, which may give emergency crew information about the user's health. In addition, the user's health insurance information may be stored using the apparatus.

Voice recording. In addition to or instead of a display, the apparatus may utilize a record voice message to provide information to the user.

Suggestion. The apparatus may suggest actions to users in response to a measured health condition.

Payments. The apparatus may be configured such that a user may make a payment using the apparatus.

Medicine reminders. The apparatus may be configured to automatically dispense medicine to the user. The medicine may be dispensed in response to a measured physiological state (e.g., detecting a potential heart attack and dispensing aspirin). The apparatus may be configured to emit a sound, vibrate, or otherwise indicate that the user should take a medicine (e.g., to reduce the risk of the user forgetting to take his or her medicine).

Data display, analysis, measurement, and recording. In some implementations, personal health data may be displayed on the device after measurement. A user may measure or record health condition data using sensors on the apparatus. The information may include but need not be limited to heart rate, blood pressure, blood oxygen, and electrocardiography. The apparatus may also analyze the health measurements and display conditions in visual graphic, which may evolve as more data is gathered.

Data output. In some embodiments, the device may convert stored measurements into periodic reports. The reports may be configured to be easy to read, compare and print or send. The device may be configured to automatically send the reports to the user's healthcare provider or family.

Server and service. The apparatus may be used with a call center that contacts users to check on condition and responding action.

Module system. The apparatus may be configured to be modular, such that the device may be attached to other accessories. In addition, the apparatus may have ports, openings, or otherwise be configured to receive and utilize accessories. For example, the apparatus may have removable or extendable sensor modules that may be swapped in and out in order to provide additional functionality. In some embodiments, the apparatus may be configured to operate as a or as part of a wearable device. For example, The apparatus may be configured as a watch and include a strap to secure the device to the user's wrist. There may be sensors disposed within the strap.

What is claimed is:

1. A method of measuring a blood pressure value of a user, the method comprising:

placing a first thumb of the user in an indented portion near one end of a top surface of a handheld physiological measuring apparatus, wherein the indented portion is formed from an electroconductive material that acts as a first electrode, and the indented portion includes at least one sensor located inside the first electrode at a bottom of the indented portion;

placing a second thumb of the user on the top surface of the handheld physiological measuring apparatus, away from the indented portion, wherein the top surface is made of the electroconductive material that acts as a second electrode of the handheld physiological monitoring device; wherein the first electrode is electrically isolated from the second electrode by an insulating spacer;

measuring an electrocardiogram signal using an electrocardiogram circuit unit including the first electrode and the second electrode;

measuring a dual pulse wave signal using a pulse circuit unit of the handheld physiological measuring apparatus, wherein the pulse circuit unit is positioned at a same location on the handheld physiological measuring apparatus as the second electrode;

calculating a pulse transit time using the electrocardiogram signal and the dual pulse wave signal;

calculating a pulse wave velocity using the electrocardiogram signal and the dual pulse wave signal;

calculating the blood pressure value using the calculated pulse transit time and the calculated pulse wave velocity; and outputting the calculated blood pressure value to the user.

2. The method of claim 1, further comprising calculating an SpO2 value using the dual pulse wave signal.

3. The method of claim 1, further comprising calculating a heart rate value using an R-R interval of the electrocardiogram signal.

4. The method of claim 1, wherein calculating the pulse transit time comprises computing a difference in time between a peak of the electrocardiogram signal and a maximum slope point of the pulse wave signal.

5. The method of claim 1, wherein the pulse wave velocity is calculated using the pulse transit time and a length of a blood vessel of the user corresponding to a distance from a heart of the user to a point where the pulse wave signal is measured.

6. The method of claim 5, wherein the length of the blood vessel is calculated using a regression equation.

7. The method of claim 5, wherein the length of the blood vessel is calculated using a movement and rotation sensor.

8. The method of claim 1, further comprising calculating an SpO2 value using the dual pulse wave signal.

9. The method of claim 1, further comprising calculating a heart rate value using at least one of the electrocardiogram signal or the dual pulse wave signal.

10. The method of claim 1, wherein the at least one sensor comprises a motion sensor, the method further comprising:

sensing a movement of the portable physiological measuring apparatus, using the motion sensor; and measuring the electrocardiogram signal and the dual pulse wave signal responsive to determining that the movement is less than a threshold value.

11. The method of claim 10, further comprising stopping measuring the electrocardiogram signal and dual pulse wave signal responsive to determining that the movement is greater than or equal to a threshold value.

12. The method of claim 10, wherein the motion sensor is selected from the group consisting of an accelerometer, a gyroscope, a shock sensor, a tilt sensor, an altimeter, a gravity sensor, and a terrestrial magnetism sensor.

13. The method of claim 1, wherein the at least one sensor is selected from the group consisting of a thermal sensor, a photo sensor, a dual photo sensor, an SpO2 sensor, and an optical sensor, and wherein the method further comprises sensing at least one parameter using the at least one sensor.

* * * * *